US012599607B2

(12) United States Patent
Löscher et al.

(10) Patent No.: US 12,599,607 B2
(45) Date of Patent: Apr. 14, 2026

(54) PHARMACEUTICAL COMPOSITIONS COMPRISING TIMOLOL

(71) Applicant: NOVALIQ GMBH, Heidelberg (DE)

(72) Inventors: Frank Löscher, Schriesheim (DE); Sonja Krösser, Heidelberg (DE); Diana Strehl, Heidelberg (DE); Bernhard Hauptmeier, Schriesheim (DE); Kirsten Eickhoff, Aschaffenburg (DE)

(73) Assignee: NOVALIQ GMBH, Heidelberg (DE)

( * ) Notice: Subject to any disclaimer, the term of this patent is extended or adjusted under 35 U.S.C. 154(b) by 0 days.

(21) Appl. No.: 18/778,226

(22) Filed: Jul. 19, 2024

(65) Prior Publication Data

US 2024/0366621 A1 Nov. 7, 2024

Related U.S. Application Data

(63) Continuation of application No. 17/041,758, filed as application No. PCT/EP2019/057429 on Mar. 25, 2019, now abandoned.

(30) Foreign Application Priority Data

Mar. 28, 2018 (EP) .................................... 18164563
Jul. 25, 2018 (EP) .................................... 18185436

(51) Int. Cl.

| | |
|---|---|
| ***A61K 31/5377*** | (2006.01) |
| ***A61K 9/00*** | (2006.01) |
| ***A61K 9/08*** | (2006.01) |
| ***A61P 27/06*** | (2006.01) |

(52) U.S. Cl.

CPC ........ *A61K 31/5377* (2013.01); *A61K 9/0048* (2013.01); *A61K 9/08* (2013.01); *A61P 27/06* (2018.01)

(58) Field of Classification Search

CPC .... A61K 31/5377; A61K 9/0048; A61K 9/08; A61P 27/06

See application file for complete search history.

(56) References Cited

U.S. PATENT DOCUMENTS

| | | | |
|---|---|---|---|
| 2,616,927 | A | 11/1952 | Kauck et al. |
| 4,452,818 | A | 6/1984 | Haidt |
| 5,077,036 | A | 12/1991 | Long |
| 5,326,566 | A | 7/1994 | Parab |
| 5,336,175 | A | 8/1994 | Mames |
| 5,370,313 | A | 12/1994 | Beard |
| 5,518,731 | A | 5/1996 | Meadows |
| 5,578,020 | A | 11/1996 | Mosley |
| 5,667,809 | A | 9/1997 | Trevino et al. |
| 5,874,469 | A | 2/1999 | Maniar et al. |
| 5,874,481 | A | 2/1999 | Weers et al. |
| 5,904,933 | A | 5/1999 | Riess et al. |
| 5,980,936 | A | 11/1999 | Krafft et al. |
| 5,981,607 | A | 11/1999 | Ding |
| 6,042,845 | A | 3/2000 | Sun et al. |
| 6,060,085 | A | 5/2000 | Osborne |
| 6,113,919 | A | 9/2000 | Reiss et al. |
| 6,140,374 | A | 10/2000 | May et al. |
| 6,159,977 | A | 12/2000 | Reeves |
| 6,177,477 | B1 | 1/2001 | George et al. |
| 6,197,323 | B1 | 3/2001 | Georgieff |
| 6,224,887 | B1 | 5/2001 | Samour et al. |
| 6,262,126 | B1 | 7/2001 | Meinert et al. |
| 6,264,990 | B1 | 7/2001 | Knepp et al. |
| 6,294,563 | B1 | 9/2001 | Garst |
| 6,335,335 | B2 | 1/2002 | Higashiyama |
| 6,372,243 | B2 | 4/2002 | Kobuch |
| 6,391,879 | B1 | 5/2002 | Reeves |
| 6,399,087 | B1 | 6/2002 | Zhang et al. |
| 6,458,376 | B1 | 10/2002 | Meadows |
| 6,486,212 | B2 | 11/2002 | Meinert |
| 6,489,367 | B1 | 12/2002 | Meinert |
| 6,528,086 | B2 | 3/2003 | Zhang |
| 6,730,328 | B2 | 5/2004 | Maskiewicz et al. |
| 7,001,607 | B1 | 2/2006 | Menz et al. |
| 7,026,359 | B1 | 4/2006 | Gross |
| 7,041,705 | B2 | 5/2006 | Mishra et al. |
| 7,063,241 | B2 | 6/2006 | Spada et al. |
| 7,074,827 | B2 | 7/2006 | Ueno |

(Continued)

FOREIGN PATENT DOCUMENTS

| | | |
|---|---|---|
| EP | 0 089 815 | 9/1983 |
| EP | 2708228 A1 | 3/2014 |

(Continued)

OTHER PUBLICATIONS

Heiden et al. Investigative Ophthalmology & Visual Science Apr. 2014, vol. 55, 453. (Year: 2014).*

Kumar et al. J Adv Pharm Tech Res, 2011; 2(3):192-194. (Year: 2011).*

A. Sah et al. (2017), Artificial Cells, Nanomedicine, and Biotechnology, 45:3, 448-459, DOI: 10.3109/21691401.2016.1160917. (Year: 2017).*

Agrahari, V. et al., "A comprehensive insight on ocular pharmacokinetics," Drug Delivery and Translational Research, vol. 6, No. 6, pp. 735-754, (2016).

Ahmed, I. et al., "Disposition of Timolol and Inulin in the Rabbit Eye Following Corneal Versus Non-Corneal Absorption," International Journal of Pharmaceutics, vol. 38, pp. 9-21, (1987).

(Continued)

*Primary Examiner* — James H Alstrum-Acevedo
*Assistant Examiner* — Manahil Mirghani Ali Abdalhameed
(74) *Attorney, Agent, or Firm* — Hoxie & Associates LLC

(57) ABSTRACT

The present invention relates to pharmaceutical composition comprising the beta 1 ($\beta_1$)-receptor blocker timolol and a liquid vehicle comprising a semifluorinated alkane. The pharmaceutical composition of the present invention may be useful for topical administration, for example ophthalmic topical administration and for use in the treatment of glaucoma, increased intraocular pressure, ocular hypertension and/or a symptom associated therewith.

21 Claims, 3 Drawing Sheets

(56) References Cited

U.S. PATENT DOCUMENTS 7,258,869 B1 8/2007 Berry et al.
7,687,455 B2 3/2010 Bonnet et al.
7,740,875 B2 6/2010 Dechow
7,776,349 B2 8/2010 Dechow et al.
8,029,977 B2 10/2011 Meinert
8,222,292 B2 7/2012 Goskonda et al.
8,328,775 B2 12/2012 Gokhale et al.
8,470,873 B2 6/2013 Chen et al.
8,492,334 B2 7/2013 Lavik et al.
8,501,800 B2 8/2013 Bowman et al.
8,614,178 B2 12/2013 Theisinger et al.
8,618,093 B2 12/2013 Chen et al.
8,748,425 B2 6/2014 Chang et al.
8,759,404 B2 6/2014 Daftary et al.
8,772,337 B2 7/2014 Pilotaz et al.
8,796,340 B2 8/2014 Theisinger et al.
8,916,157 B2 12/2014 Krause et al.
8,986,738 B2 3/2015 Meinert
9,005,626 B2 4/2015 Seigfried
9,023,898 B2 5/2015 Wong et al.
9,241,900 B2 1/2016 Wilson
9,308,262 B2 4/2016 Günther et al.
9,757,459 B2 9/2017 Theisinger et al.
9,757,460 B2 9/2017 Günther et al.
9,770,508 B2 9/2017 Günther et al.
9,968,678 B2 5/2018 Theisinger et al.
10,045,996 B2 8/2018 Theisinger et al.
10,045,997 B2 8/2018 Chen et al.
10,058,615 B2 8/2018 Günther et al.
10,064,944 B2 9/2018 Wilson
10,123,904 B2 11/2018 Chauhan et al.
10,130,707 B2 11/2018 Günther et al.
10,273,298 B2 4/2019 Günther et al.
10,369,117 B2 8/2019 Günther et al.
10,449,164 B2 10/2019 Günther et al.
10,507,132 B2 12/2019 Graf et al.
10,525,062 B2 1/2020 Theisinger et al.
10,543,121 B2 1/2020 Labombarbe et al.
10,555,953 B2 2/2020 Theisinger et al.
10,576,154 B2 3/2020 Günther et al.
10,682,315 B2 6/2020 Scherer et al.
10,813,976 B2 10/2020 Löscher et al.
10,813,999 B2 10/2020 Günther et al.
11,154,513 B2 10/2021 Scherer et al.
11,160,865 B2 11/2021 Theisinger et al.
11,273,174 B2 3/2022 Löscher et al.
11,278,503 B2 3/2022 Günther et al.
11,285,163 B2 3/2022 Shah et al.
11,324,757 B2 5/2022 Theisinger et al.
11,357,738 B2 6/2022 Scherer et al.
11,400,132 B2 8/2022 Löscher et al.
11,413,323 B2 8/2022 Leo et al.
11,576,893 B2 2/2023 Löscher et al.
11,583,513 B2 2/2023 Günther et al.
11,684,589 B2 6/2023 Günther et al.
11,723,861 B2 8/2023 Günther et al.
11,844,836 B2 12/2023 Günther et al.
11,896,559 B2 2/2024 Günther et al.
11,987,623 B2 5/2024 Günther et al.
12,005,033 B2 6/2024 Günther et al.
RE50,060 E 7/2024 Graf et al.
12,059,449 B2 8/2024 Leo et al.
12,128,010 B2 10/2024 Scherer et al.
12,150,955 B2 11/2024 Loscher et al.
12,226,422 B2 2/2025 Löscher et al.
2002/0004063 A1 1/2002 Zhang
2002/0128527 A1 9/2002 Meinert
2002/0198266 A1 12/2002 Meinert
2003/0018044 A1 1/2003 Peyman
2003/0027833 A1 2/2003 Cleary et al.
2003/0170194 A1 9/2003 Piotrowiak
2004/0044045 A1 3/2004 Burk
2004/0082660 A1 4/2004 Ueno
2004/0101551 A1 5/2004 Selzer
2004/0265362 A1 12/2004 Susilo
2004/0266702 A1 12/2004 Dawson et al.
2005/0075407 A1 4/2005 Tamarkin et al.
2005/0079210 A1 4/2005 Gupta
2005/0175541 A1 8/2005 Lanza et al.
2005/0274744 A1 12/2005 Spada et al.
2005/0288196 A1 12/2005 Horn
2006/0009522 A1 1/2006 Dana et al.
2006/0153905 A1 7/2006 Carrara et al.
2007/0238732 A1 10/2007 Graham et al.
2008/0019926 A1 1/2008 Krafft et al.
2008/0050335 A1 2/2008 Faour et al.
2008/0089923 A1 4/2008 Burkstrand et al.
2008/0153909 A1 6/2008 Dana et al.
2008/0207537 A1 8/2008 Turner et al.
2008/0234389 A1 9/2008 Mecozzi et al.
2008/0254106 A1 10/2008 Bell
2008/0260656 A1 10/2008 Mallard
2009/0149546 A1 6/2009 Chang
2009/0169601 A1 7/2009 Koch et al.
2009/0226875 A1 9/2009 Meinert
2010/0006600 A1 1/2010 Dascanio
2010/0008996 A1 1/2010 Meinert
2010/0016814 A1 1/2010 Gokhale et al.
2010/0189765 A1 7/2010 Erickson et al.
2010/0226997 A1 9/2010 Bowman et al.
2010/0261646 A1 10/2010 Lavik et al.
2010/0274215 A1 10/2010 Wong et al.
2011/0223208 A1 9/2011 Hill et al.
2011/0269704 A1 11/2011 Seigfried
2012/0010280 A1 1/2012 Aleo et al.
2012/0095097 A1 4/2012 Tabuchi et al.
2012/0238639 A1 9/2012 Theisinger et al.
2012/0244177 A1 9/2012 Theisinger et al.
2013/0011484 A1 1/2013 Bevier
2013/0046014 A1 2/2013 Theisinger
2013/0084250 A1 4/2013 Hagedorn et al.
2013/0266652 A1 10/2013 Theisinger et al.
2013/0303473 A1 11/2013 Wilson
2013/0336557 A1 12/2013 Cruzat et al.
2014/0004197 A1 1/2014 Theisinger et al.
2014/0100180 A1 4/2014 Günther et al.
2014/0140942 A1 5/2014 Günther et al.
2014/0186350 A1 7/2014 Ghosh et al.
2014/0369993 A1 12/2014 Günther et al.
2015/0045282 A1 2/2015 Elsohly et al.
2015/0224064 A1 8/2015 Günther et al.
2015/0238605 A1 8/2015 Günther et al.
2016/0000941 A1 1/2016 Keller et al.
2016/0101178 A1* 4/2016 Wilson .................... A61P 27/02
514/420
2016/0159902 A1 6/2016 Günther et al.
2016/0243189 A1 8/2016 Gu et al.
2016/0303031 A1 10/2016 El Achkar et al.
2017/0020726 A1 1/2017 Labombarbe et al.
2017/0087100 A1 3/2017 Scherer et al.
2017/0087101 A1 3/2017 Scherer et al.
2017/0143832 A1 5/2017 Günther et al.
2017/0182060 A1 6/2017 Wiedersberg et al.
2017/0216204 A1 8/2017 Theisinger et al.
2017/0348285 A1 12/2017 Hellstron
2018/0360908 A1 12/2018 Beier et al.
2019/0328717 A1 10/2019 Günther et al.
2019/0343793 A1 11/2019 Günther et al.
2020/0023035 A1 1/2020 Löscher
2020/0060987 A1 2/2020 Gunther et al.
2020/0129543 A1 4/2020 Löscher et al.
2020/0188318 A1 6/2020 Günther et al.
2020/0206241 A1 7/2020 Theisinger et al.
2020/0246463 A1 8/2020 Günther et al.
2020/0268682 A1 8/2020 Günther et al.
2020/0338015 A1 10/2020 Scherer et al.
2021/0023166 A1 1/2021 Löscher et al.
2021/0069014 A1 3/2021 Löscher et al.
2021/0106558 A1 4/2021 Löscher et al.
2021/0121471 A1* 4/2021 Löscher ............. A61K 31/5377
2021/0228595 A1 7/2021 Löscher et al.
2021/0236591 A1 8/2021 Leo et al.
2021/0315832 A1 10/2021 Scherer et al.
2021/0346313 A1 11/2021 Beier et al.

(56) References Cited

U.S. PATENT DOCUMENTS

| | | | |
|---|---|---|---|
| 2022/0008397 A1 | 1/2022 | Xu et al. | |
| 2022/0031844 A1 | 2/2022 | Mauden et al. | |
| 2022/0079925 A1 | 3/2022 | Günther et al. | |
| 2022/0143137 A1 | 5/2022 | Witt et al. | |
| 2022/0226426 A1 | 7/2022 | Löscher et al. | |
| 2022/0226427 A1 | 7/2022 | Leo et al. | |
| 2022/0354926 A1 | 11/2022 | Löscher et al. | |
| 2022/0362382 A1 | 11/2022 | Loscher et al. | |
| 2022/0370377 A1 | 11/2022 | Scherer et al. | |
| 2023/0043641 A1 | 2/2023 | Beier et al. | |
| 2023/0139672 A1 | 5/2023 | Theisinger et al. | |
| 2023/0181679 A1 | 6/2023 | Haisser et al. | |
| 2023/0330056 A1 | 10/2023 | Günther et al. | |
| 2023/0398065 A1 | 12/2023 | Günther et al. | |
| 2024/0245625 A1 | 7/2024 | Günther et al. | |

FOREIGN PATENT DOCUMENTS

| | | | | |
|---|---|---|---|---|
| JP | 2012-250951 | 12/2012 | | |
| WO | WO 2002/096432 | 12/2002 | | |
| WO | WO 2003/088973 | 10/2003 | | |
| WO | WO 2003/099258 | 12/2003 | | |
| WO | WO 2008/136034 | 11/2008 | | |
| WO | WO 2008/157614 | 12/2008 | | |
| WO | WO-2008157614 A2 * | 12/2008 | .......... | A61K 9/0048 |
| WO | WO 2010/146536 | 12/2010 | | |
| WO | 2011/112669 A1 | 9/2011 | | |
| WO | WO 2016/063184 | 4/2016 | | |
| WO | WO 2016/082644 | 6/2016 | | |
| WO | 2018/033854 A1 | 2/2018 | | |

OTHER PUBLICATIONS

Agarwal, P. et al., "Semifluorinated alkane based systems for enhanced corneal penetration of poorly soluble drugs," International Journal of Pharmaceutics, vol. 538, No. 1-2, pp. 119-129, (2018).

Bardin, L. et al., "Long-Range Nanometer-Scale Organization of Semifluorinated Alkane Monolayers at the Air/Water Interface," Langmuir, vol. 27, pp. 13497-13505, (2011).

Bertilla, S. et al., "Semifluorinated Alkanes as Stabilizing Agents of Fluorocarbon Emulsions," Springer, vol. 12, 24 pages, (2005).

Costa Gomes, M. et al., "Solubility of dioxygen in seven fluorinated liquids," Journal of Fluorine Chemistry, vol. 125, pp. 1325-1329, (2004).

Davies, N., "Biopharmaceutical Considerations in Topical Ocular Drug Delivery," Clinical and Experimental Pharmacology and Physiology, vol. 27, pp. 558-562, (2000).

Dembinski, R. et al., "Semi-fluorinated Alkanes as Carriers for Drug Targeting in Acute Respiratory Failure," Experimental Lung Research, vol. 36, pp. 499-507, (2010).

Deschamps, J. et al., "Solubility of oxygen, carbon dioxide and water in semifluorinated alkanes and in perfluorooctylbromide by molecular simulation," Journal of Fluorine Chemistry, Elsevier, vol. 125, No. 3, (2004).

Dias, A. et al., "Solubility of oxygen in liquid perfluorocarbons," Fluid Phase Equilibria, vol. 222-223, pp. 325-330, (2004).

Dutescu, R. et al., "Semifluorinated alkanes as a liquid drug carrier system for topical ocular drug delivery," European Journal of Pharmaceutics and Biopharmaceutics, vol. 88, No. 1, 2 pages, (2014), Abstract Only.

English-language machine translation of EP0670159 (A1) issued in U.S. Appl. No. 14/122,025 on Apr. 1, 2015, 10 pages.

English-language machine translation of JP 2012-250951 (A), 13 pages.

"Evo-Tears—Gebrauchsanweisung," May 2015, retrieved from the Internet, date retrieved: Jun. 26, 2018, 2 pages, URL: http://video. aporot.de/docs/11213615.pdf.

Freiburger Dokumentenserver (FreiDok), Albert-Ludwigs-Unversität Freiburg, retrieved from http://www.freidok.uni-freiburg. de/volltexte/5682/, retrieved on Feb. 5, 2014, 2 pages.

Gehlsen. U. et al., "Cyclosporine A using F4H5 as liquid drug carrier is effective in treating experimental dry-eye disease," Investigative Ophthalmology & Visual Science, vol. 56, No. 319, 2 pages, (2015), Abstract Only.

Gehlsen, U. et al., "A semifluorinated alkane (F4H5) as novel carrier for cyclosporine A: a promising therapeutic and prophylactic option for topical treatment of dry eye," Graefe's Arch. Clin. Exp. Ophthalmol., vol. 255, No. 4, pp. 767-775, (2017).

Gehlsen, U. et al., "Omega-3 Fatty Acids Using F6H8-Carrier as Topical Therapy in Experimental Dry-Eye Disease," Investigative Ophthalmology & Visual Science, vol. 57, p. 417, 1 page, (2016), Abstract Only.

German, E. et al., "Reality of drop size from multi-dose eye drop bottles: is it cause for concern?" Eye, vol. 13, pp. 93-100, (1999).

Hardung, H., "Semifluorierte und perfluorierte Verbindungen zur topischen und parenteralen Anwendung," 2008, English Language Abstract, 2 pages, retrieved from https://freidok.uni-freiburg.de/data/5682 (retrieved on Jul. 10, 2017).

"Highlights of Prescribing Information: Zioptan," pp. 1-11, (2014), https://www.accessdata.fda.gov/drugsatfda_docs/label/2015/202514s003s004lbl.pdf.

Hoerauf, H. et al., "Combined Use of Partially Fluorinated Alkanes, Perfluorocarbon Liquids and Silicone Oil: An Experimental Study," Graefe's Archive for Clinical and Experimental Ophthalmology, vol. 239, No. 5, pp. 373-381, (2001).

Holm, R. et al., "A novel excipient, 1-perfluorohexyloctane shows limited utility for the oral delivery of poorly water-soluble drugs," European Journal of Pharmaceutical Sciences, vol. 42, pp. 416-442, (2011).

Kaercher, T. et al., "NovaTears® as new Therapy in Dry Eye Results from three prospective, multicenter, non-interventional studies in different patient populations," TFOS Conference (Tear Film & Ocular Surface), Sep. 7-10, 2016, Montpellier, France, Poster Session II, Poster No. 60, 1 page.

Kociok, N. et al., "Influence on Membrane-Mediated Cell Activation by Vesicles of Silicone Oil or Perfluorohexyloctane," Graefe's Archive for Clinical and Experimental Ophthalmology, vol. 243, pp. 345-358, (2005).

Kumar, S. et al., "Reduction in drop size of ophthalmic topical drop preparations and the impact of treatment," Journal of Advanced Pharmaceutical Technology & Research, vol. 2, No. 3, pp. 192-194, (2011).

Lallemand, F. et al., "Cyclosporine A delivery to the eye: a pharmaceutical challenge," European Journal of Pharmaceutics and Biopharmaceutics, vol. 56, No. 3, 1 page, (2003), Abstract Only.

"Latanoprost (Xalatan®)," Chemical Abstracts, CAS Registry No. 130209-82-4, retrieved from the Internet, date accessed: Mar. 21, 2022, 5 pages, URL:<https://www.chemicalbook.com/CASEN_130209-82-4.htm>.

Lynch, M. et al., "Reduction of Phenylephrine Drop Size in Infants Achieves Equal Dilation With Decreased Systemic Absorption," Arch Ophthalmol, vol. 105, 2 pages, (1987).

Meinert, H. et al., "Semifluorinated Alkanes—A New Class of Compounds with Outstanding Properties for Use in Ophthalmology," European Journal of Ophthalmology, vol. 10, No. 3, pp. 189-197, (2000).

Messmer, E. et al., "Semifluorinated Alkanes as a Therapy for Meibomian Gland Dysfunction Results of a prospective, multi-centered observational study," Presentation, DOG-Kongress, Sep. 29, 2016-Oct. 2, 2016, Berlin DOG (Deutsche Ophtalmologische Gesellschaft), Poster No. PSa03-02, English Translation, 6 pages.

Messmer, E. et al., "Semifluorinated Alkanes as a Therapy for Meibomian Gland Dysfunction Results of a prospective, multi-centered observational study," Presentation, DOG-Kongress, Sep. 29, 2016-Oct. 2, 2016, Berlin DOG (Deutsche Ophtalmologische Gesellschaft), Ophthalmologe, Aug. 2016, Poster No. PSa03-02, English Translation of Abstract, p. 138.

O'rourke, M. et al., "Enhancing Delivery of Topical Ocular Drops," Cataract & Refractive Surgery Today Europe, 2 pages, (2016).

Rathore, K. et al., "Timolol Maleate A Gold Standard Drug in Glaucoma Used as Ocular Films and Inserts: An Overview," International Journal of Pharmaceutical Sciences Review and Research, vol. 3, No. 1, 8 pages, (2010).

(56) References Cited

OTHER PUBLICATIONS

Santvliet, L. et al., "Determinants of Eye Drop Size," Survey of Ophthalmology, vol. 49, No. 2, pp. 197-213, (2004).
Scherer, D. et al., "Eyesol: A Novel Topical Ocular Drug Delivery System for Poorly Soluble Drugs," Drug Development & Delivery, vol. 13, No. 1, pp. 40-44, (2013).
"Semifluorinated alkane technology brings advantages for topical therapy," Ophthalmology Times, 2016, pp. 1-2, http://www.ophthalmologytimes.com/ophthalmology/semifluorinated-alkane-technology-brings-advantages-topical-therapy.
Steven, P. et al., "Semifluorinated Alkane Eye Drops for Treatment of Dry Eye Disease—A Prospective, Multicenter Noninterventional Study," Journal of Ocular Pharmacology and Therapeutics, vol. 31, No. 8, pp. 498-503, (2015).
Steven, P. et al., "Semifluorinated Alkane Eye Drops for Treatment of Dry Eye Disease Due to Meibomian Gland Disease," Journal of Ocular Pharmacology and Therapeutics, vol. 33, No. 9, pp. 1-8, (2017).
Steven, P. et al., "Semifluorinated Alkane Eye Drops for Treatment of Dry Eye Disease—A Prospective, Multicenter Noninterventional Study," Investigative Ophthalmology & Visual Science, vol. 56, No. 4493, 1 page, (2015), Abstract Only.
TIMOPTIC®, NDA 18-086/S-070 / NDA 18-086/S-072, Merck & Co, Inc, 11 pages, (2005).
Van Der Heiden, H. et al., "Plasma and ocular pharmacokinetic study comparing 3 uL micro-drop to typical 40 µL drop volume of timolol 0.5% in pigmented rabbits," ARVO Annual Meeting Abstract, Investigative Ophthalmology & Visual Science, vol. 55, 1 page, (2014).
Wong, D. et al., "Perfluorocarbons and Semifluorinated Alkanes," Seminars in Ophthalmology, vol. 15, No. 1, pp. 25-35, (2000).
Wirta, D. et al., "A Clinical Phase II Study to Assess Efficacy, Safety and Tolerability of Waterfree Cyclosporine Formulation for the Treatment of Dry Eye Disease," Ophthalmology, vol. 126, pp. 792-800, (2019).
"EvoTears, Product Description," 2017, Accessed Online: Dec. 27, 2023, URL: https://evotears.com/at/das-produkt/.
"Novaliq Announces Positive Topline Results of Phase 2 Clinical Trial Evaluating CyclASol® in Adults with Moderate to Severe Dry Eye Disease," Businesswire, Jan. 5, 2017, URL: <https://www.businesswire.com/ news/home/20170105005211/en/Novaliq-Announces-Positive-Topline-Results-Phase-2>.
"Novaliq begins Phase 2 trial of Cyclasol for dry eye disease," Optometry Times, vol. 8, No. 3, (2016), p. 24.
"Novaliq GmbH Begins Phase II Clinical Trial of Cyclasol for the Treatment of Moderate to Severe Dry Eye Disease," (online), 5 pages, (2016); retrieved on Jan. 8, 2021 from the Internet: https://www.biospace.com/article/releases/novaliq-gmbh-begins-phase-ii-clinical-trial-of-cyclasol-for-the-treatment-of-moderate-to-severe-dry-eye-disease-/.
"PharmaNews," Kompass Ophthalmologie, vol. 2, No. 2, pp. 98-99, (2016).
"Topical drug dosage forms for eye conditions," The Pharmaceutical Journal, (Pharmaceutical Press, May 31, 2017), available at https://pharmaceutical-journal.com/article/Id/topical-drug-dosage-forms-for-eye-conditions.
Ahmed, S. et al., "Ocular Drug Delivery: a Comprehensive Review," AAPS PharmSciTech, vol. 24, No. 66, pp. 1-29, (2023).
English language machine translation for "PharmaNews," Kompass Ophthalmologie, vol. 2, No. 2, pp. 98-99, (2016).
Majumdar, S. et al. "A Low Concentration of Tacrolimus/Semifluorinated Alkane (SFA) Eyedrop Suppresses Intraocular Inflammation in Experimental Models of Uveitis," Current Molecular Medicine, vol. 17, No. 3, pp. 211-220, (2017).
Meinert, H. et al., "The Use of Semifluorinated Alkanes in Blood-Substitutes," Biomaterials, Artificial Cells, and Immobilization Biotechnology, vol. 21, No. 5, pp. 583-595, (1993).
Sheppard, J. et al., "A Water-free 0.1% Cyclosporine A Solution for Treatment of Dry Eye Disease: Results of the Randomized Phase 2B/3 ESSENCE Study," Cornea, vol. 40, No. 10, pp. 1290-1297, (2021).
Toris, C. et al., "Update on the Mechanism of Action of Topical Prostaglandins for Intraocular Pressure Reduction," NIH Public Access, Author Manuscript, available in PMC 2009, 18 pages, front page states: Published in final edited form as: Surv Ophthalmol. Nov. 2008 ; 53(Suppl1): S107-S120. doi:10.1016/j.survophthal.2008.08.010.
Torkildsen, G. et al., "A Clinical Phase 2 Study to Assess Safety, Efficacy, and Tolerability of CyclASol for the Treatment of Dry Eye Disease," Poster Presentation at American Academy of Ophthalmology (AAO), New Orleans 2017.

* cited by examiner

PHARMACEUTICAL COMPOSITIONS COMPRISING TIMOLOL

CROSS-REFERENCE TO RELATED APPLICATIONS

This application is a continuation of application Ser. No. 17/041,758, filed on Sep. 25, 2020, which is a U.S. National Stage application under 35 U.S.C. § 371 of International Application No. PCT/EP2019/057429, filed on Mar. 25, 2019, which claims priority to and the benefit of European Application No. 18164563.1, filed on Mar. 28, 2018, and European Application No. 18185436.5, filed on Jul. 25, 2018, the contents of each of which are hereby incorporated by reference in their entireties.

BACKGROUND

The present invention relates to a pharmaceutical composition comprising a) timolol and/or a pharmaceutically acceptable salt thereof and b) a liquid vehicle comprising a semifluorinated alkane. The pharmaceutical composition of the present invention may be useful for topical administration, especially ophthalmic topical administration.

Pharmaceutical compositions in liquid form represent one of the preferred types of drug formulations. Certain routes of topical administration, such as ophthalmic administration, typically require the liquid form in order to provide for an efficient delivery of the active ingredient and a patient-friendly mode of use.

The simplest type of liquid formulation is a solution, such as an aqueous solution of the active pharmaceutical ingredient. In certain cases, however, the development of a more complex formulation such as a suspension may be considered. For example, if a drug substance is very poorly soluble in aqueous or other biocompatible solvent systems, or if it is hydrolytically labile, a simple solution may not be feasible or represent the best choice.

Timolol belongs to a class of compounds named beta-blockers. Timolol in its oral form is used to treat high blood pressure and prevent heart attacks. In its ophthalmic form is used to treat open-angle glaucoma.

Beta-blockers act by blocking beta-receptors at the level of the ciliary body and by reducing the aqueous humour production, thereby reducing the intraocular pressure (IOP). Two types of topical beta-blockers are available for use in the treatment of glaucoma: non-selective beta-blockers, which block both beta 1 ($\beta_1$)- and beta 2 ($\beta_2$)-adrenoceptors; and cardio-selective beta blockers, which block only beta 1-receptors.

Timolol is a non-selective beta-adrenergic receptor antagonist. Timolol, when applied topically to the eye, has the action of reducing elevated, as well as normal, intraocular pressure, whether or not accompanied by glaucoma. Elevated intraocular pressure is a major risk factor in the pathogenesis of glaucomatous visual field loss and optic nerve damage.

Increased intraocular pressure is a frequent disorder of the eye which is often associated with optic nerve damage, in which case the disease is glaucoma. In the absence of optic nerve damage, the condition is referred to as ocular hypertension.

Normal intraocular pressure is usually defined as being in the range from 10 to 21 mmHg. The pressure results predominantly from the balance between the production rate and the drainage rate of the aqueous humour in the eye. In addition, it is influenced by the corneal thickness and rigidity. The intraocular pressure typically fluctuates around about 15 to 16 mmHg with amplitudes of up to 6 mmHg. For example, it usually decreases in the night due to a decreased production of aqueous humour. It also responds to various physiological factors such as exercise, heart rate, respiration, fluid intake, as well as certain types of systemic or topical drugs.

The aqueous humour is produced by the ciliary bodies of the eye, from where it flows into the posterior chamber. The composition of the aqueous humour is very similar to that of blood plasma but differs from the latter by a lower protein content. Its main constituents are water (99%), electrolytes (inorganic ions to maintain the physiological pH), low amounts of albumin and β-globulins, ascorbate, glucose, lactate, and amino acids.

From the posterior chamber, the aqueous humour is distributed via the pupil of the iris into the anterior chamber of the eye. From here, it flows through the so-called trabecular meshwork, which is a spongy tissue area lined by trabeculocytes whose main function is to drain the humour into a set of tubes called Schlemm's canal, from where the humour enters the blood circulation. The humour flow from the trabecular meshwork into the Schlemm's canal occurs via two different routes: either directly via the aqueous vein to the episcleral vein, or indirectly via collector channels to the episcleral vein by intrascleral plexus. This trabecular outflow pathway accounts for the major fraction of drained aqueous humour. In addition, there exists a second major drainage pathway which is the uveoscleral outflow, which is relatively independent of the intraocular pressure and normally accounts for only 5 to 10% of the aqueous humour drainage in healthy humans.

Ophthalmic timolol is available in the market as a solution (liquid) and an extended-release (long-acting) gel-forming solution (liquid that thickens to a gel when instilled in the eye). Timolol eye drops are usually instilled once or twice a day, at evenly spaced intervals, until pressure in the eye is controlled (about 4 weeks). Then it may be instilled once a day. Timolol gel-forming solution is usually instilled once a day.

Timoptic® (timolol maleate ophthalmic solution) is indicated in the treatment of elevated intraocular pressure in patients with ocular hypertension or open-angle glaucoma. Timoptic® is supplied as a sterile, isotonic, buffered aqueous solution of timolol maleate in two dosage strengths. Each mL of Timoptic® 0.25% contains 2.5 mg of timolol (3.4 mg of timolol maleate). Each mL of Timoptic® 0.5% contains 5 mg of timolol (6.8 mg of timolol maleate). As inactive ingredients, monobasic and dibasic sodium phosphate, sodium hydroxide, water for injection and benzalkonium chloride 0.01% as preservative are included.

The effects of timolol maleate on the intraocular pressure in patients with chronic open angle glaucoma compared to epinephrine or pilocarpine has been described in Drugs 1979 January; 17(1):38-55.

U.S. Pat. No. 6,335,335 B2 describes a method to promote penetration of a beta blocker into the eye and to improve the retention of the beta blocker in the ocular tissues by incorporating a C3-C7 fatty acid into an eye drop containing the beta blocker. Highly water soluble components find in the highly hydrophobic corneal epithelium a barrier to the penetration of the components into the eye. It is therefore necessary to instill the eye drop containing the components in high dose or many times, so that a sufficient amount of the components penetrates in the eye tissues for lowering an intraocular pressure. However, in order to separate from the systemic effect of the beta blocker, to get more effect on lowering intraocular pressure and to get the prolonged action of the beta blocker, it is preferable to promote penetration of the drugs into the eye and to prolong retention of the drug in the eye than to instill a high amount of the eye drop and instill many times.

It is an object of the present invention to provide a novel pharmaceutical formulation comprising timolol and/or a pharmaceutically acceptable salt thereof, which can be useful as a medicament, particularly for topical applications. It is a further object of the present invention to find a treatment of increased intraocular pressure, e.g. in association with open-angle glaucoma or ocular hypertension, which overcomes at least one of the limitations or disadvantages associated with prior art formulations.

A further object of the present invention is to provide liquid formulations of timolol and/or a pharmaceutically acceptable salt thereof which is effective in decreasing intraocular pressure at reduced target dosage compared to commercial timolol solutions.

Further objects of the invention will become clear on the basis of the following description, examples, and patent claims.

SUMMARY OF THE INVENTION

In a first aspect, the present invention provides a pharmaceutical composition comprising:

(a) timolol and/or a pharmaceutically acceptable salt thereof, and (b) a liquid vehicle comprising a semifluorinated alkane.

In a second aspect, the present invention provides the composition of the first aspect of the invention for use as medicament, more specifically for the treatment of glaucoma, increased intraocular pressure, ocular hypertension and/or a symptom associated therewith.

In a further aspect, the present invention provides a method for the treatment of glaucoma, increased intraocular pressure, ocular hypertension and/or a symptom associated therewith, comprising administering to the eye of a subject in need thereof a pharmaceutical composition according to the first aspect of the present invention.

In yet a further aspect, the present invention provides a kit comprising the pharmaceutical composition according to the first or second aspect of the invention and a container for holding the pharmaceutical composition.

DETAILED DESCRIPTION OF THE INVENTION

Figure 1:
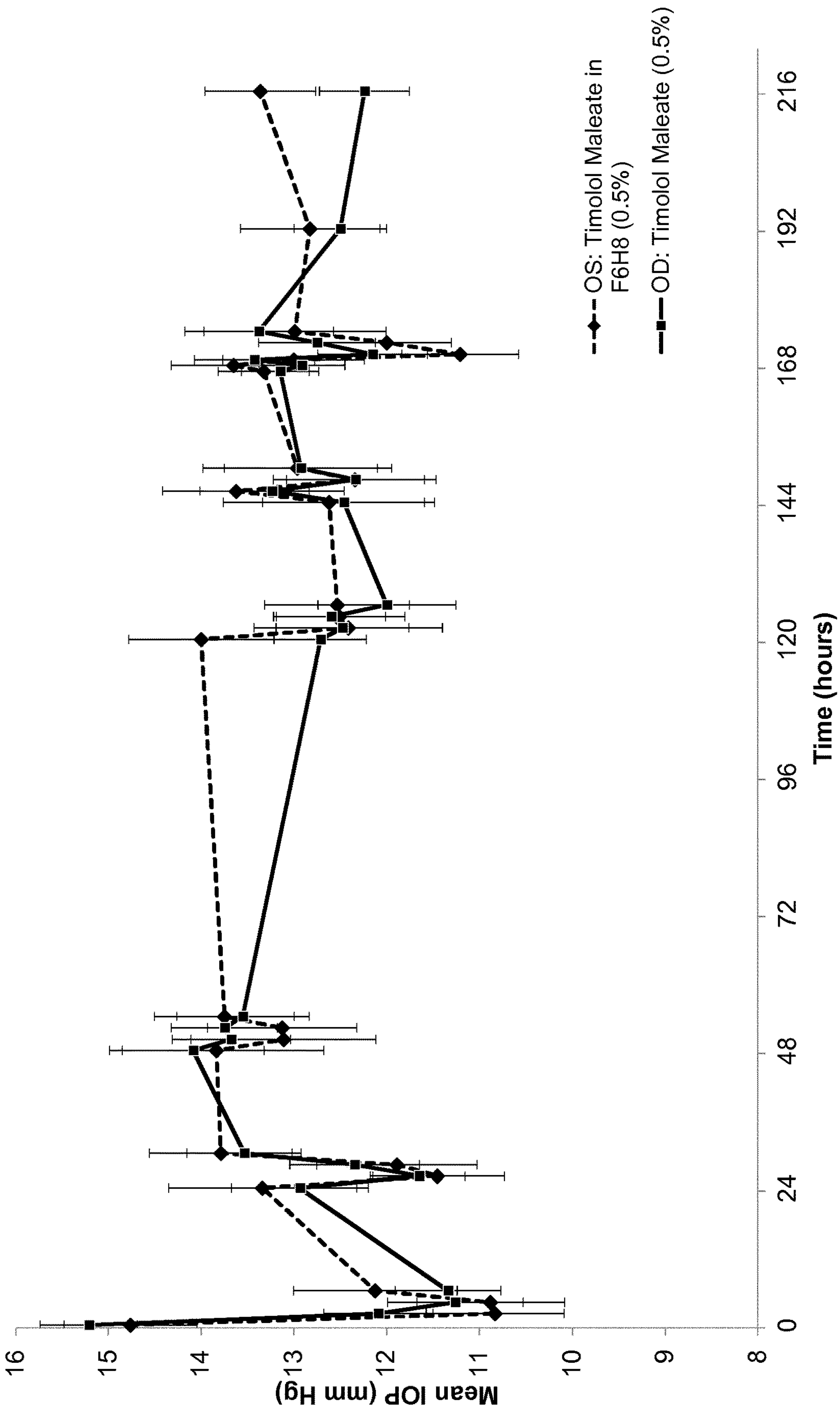
FIG. 1 is a graphical representation of the results of the measurement of the in-vivo intraocular pressure study according to Example 2 below in which a suspension of timolol at a concentration of 0.5% (w/v) in 1-perfluorohexyl-octane (F6H8) is administered once a day.

It has been found by the inventors that the composition of the invention surprisingly overcomes several drawbacks of previously known formulations of timolol.

In a first aspect, the present invention provides a pharmaceutical composition comprising:

(a) timolol and/or a pharmaceutically acceptable salt thereof, and (b) a liquid vehicle comprising a semifluorinated alkane.

The pharmaceutical composition according to the present invention comprises as a first constituent (a) timolol and/or a pharmaceutically acceptable salt of timolol. The compound timolol, IUPAC name (2S)-1-(tert-butylamino)-3-{[4-(morpholin-4-yl)-1,2,5-thiadiazol-3-yl]oxy}propan-2-ol, as used herein is of structural formula (Ia)

(Ia)

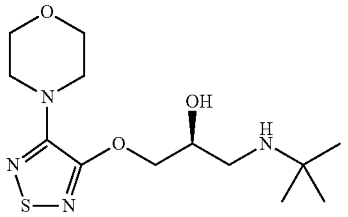

with the chemical formula $C_{13}H_{24}N_4O_3S$ and molecular mass of 316.42 g/mol. Timolol is commercially available in form of its free base ((S)-timolol base) as described and shown by formula (Ia) above, as well as in the form of pharmaceutically acceptable salts such as, for example timolol maleate of formula (Ib), IUPAC name (2S)-1-(tert-butylamino)-3-[(4-morpholin-4-yl-1,2,5-thiadiazol-3-yl)oxy]propan-2-ol maleate salt, molecular mass of 432.492 g/mol.

(Ib)

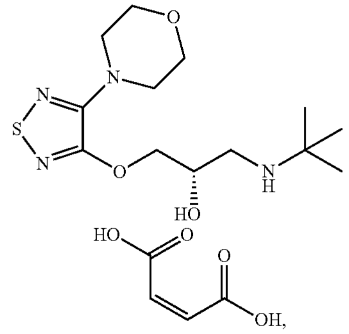

Timolol free base can also be provided in form of (S)-timolol base hemihydrate, as represented in formula (Ic) and having chemical formula $C_{26}H_{50}N_8O_7S_2$ and molecular mass of 650.324 g/mol.

(Ic)

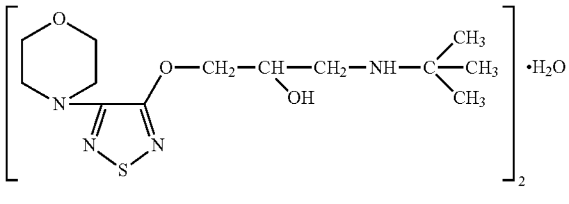

The pharmaceutical composition comprises timolol and/or a pharmaceutically acceptable salt of timolol, which means that the composition may comprise timolol in form of its free base as, for example shown in formula (Ia), either alone or in combination with one or a mixture of different pharmaceutically acceptable salts of timolol. Furthermore, the present pharmaceutical composition may comprise timolol in form of a salt, such as timolol maleate of formula (Ib) either alone or in form of a mixture with other pharmaceutically acceptable salts of timolol as described above.

In a preferred embodiment of the present invention, however, the pharmaceutical composition of the present invention comprises timolol in form of timolol maleate or (S)-timolol base hemihydrate. In another preferred embodiment, the pharmaceutical composition of the present invention comprises as component a) one selected from timolol maleate and (S)-timolol base hemihydrate. Preferably, the pharmaceutical composition of the present invention comprises as component a) timolol maleate. More preferably, the pharmaceutical composition of the present invention comprises as component a) the levo-isomer of timolol maleate.

Preferably, the timolol and/or another pharmaceutically acceptable salt of timolol as described above is present in the pharmaceutical composition according to present invention in a therapeutically effective amount. The term "a therapeutically effective amount" as used herein refers to a dose, concentration or strength which is useful for producing a desired pharmacological effect.

As a second constituent (b), the pharmaceutical composition according to the present invention comprises a liquid vehicle comprising a semifluorinated alkane. Some of the key advantages of the present invention are brought about by the presence of a semifluorinated alkane in the composition, functioning as a liquid vehicle for forming either a solution, dispersion or a suspension. The term 'semifluorinated alkane' as used herein means a compound in which a perfluorinated linear or branched, preferably linear hydrocarbon segment is attached to a linear or branched, preferably linear hydrocarbon segment.

In preferred embodiments, however, the pharmaceutical composition of the present invention or, more specifically, the liquid vehicle of the pharmaceutical composition of the present invention comprises a semifluorinated alkane of the general formula (II)

$$CF_3(CF_2)_n(CH_2)_mCH_3 \quad \text{(II)},$$

wherein the index n is an integer selected from 2 to 10, and m is an integer selected from 2 to 10. Preferably, the liquid vehicle of the pharmaceutical composition of the present invention comprises a semifluorinated alkane of the general formula (II) wherein the index n is an integer selected from 3 to 7, and m is an integer selected from 4 to 7, more preferably wherein the index n is an integer selected from 3 to 5, and m is an integer selected from 4 to 7.

Accordingly, said semifluorinated alkane as used in the composition of the present invention may preferably be selected from $CF_3(CF_2)_3$—$(CH_2)_4CH_3$ (F4H5), $CF_3(CF_2)_3$—$(CH_2)_5CH_3$ (F4H6), $CF_3(CF_2)_3$—$(CH_2)_6CH_3$ (F4H7), $CF_3(CF_2)_3$—$(CH_2)_7CH_3$ (F4H8), $CF_3(CF_2)_4$—$(CH_2)_4CH_3$ (F5H5), $CF_3(CF_2)_4$—$(CH_2)_5CH_3$ (F5H6), $CF_3(CF_2)_4$—$(CH_2)_6CH_3$ (F5H7), $CF_3(CF_2)_4$—$(CH_2)_7CH_3$ (F5H8), $CF_3(CF_2)_5$—$(CH_2)_4CH_3$ (F6H5), $CF_3(CF_2)_5$—$(CH_2)_5CH_3$ (F6H6), $CF_3(CF_2)_5$—$(CH_2)_6CH_3$ (F6H7), $CF_3(CF_2)_5$—$(CH_2)_7CH_3$ (F6H8), $CF_3(CF_2)_7$—$(CH_2)_7CH_3$ (F8H8). More preferably, said semifluorinated alkane may be selected from $CF_3(CF_2)_3$—$(CH_2)_4CH_3$ (F4H5), $CF_3(CF_2)_5$—$(CH_2)_5CH_3$ (F6H6), $CF_3(CF_2)_5$—$(CH_2)_7CH_3$ (F6H8) and $CF_3(CF_2)_5$—$(CH_2)_9CH_3$ (F6H10). Most preferably, said semifluorinated alkane may be selected from $CF_3(CF_2)_3$—$(CH_2)_4CH_3$ (F4H5) and $CF_3(CF_2)_5$—$(CH_2)_7CH_3$ (F6H8).

An alternative nomenclature for the specified semifluorinated alkanes as noted in parentheses below and as may be further used herein, is based on the general formula FnHm, wherein F means the linear perfluorinated hydrocarbon segment, H means the linear non-fluorinated hydrocarbon segment and n, m is the number of carbon atoms of the respective segment. For example, F4H5 may be used to denote 1-perfluorobutyl-pentane or $CF_3(CF_2)_3$—$(CH_2)_4CH_3$ (which may be also, alternatively expressed as formula $F(CF_2)_4(CH_2)_5H$), which has a linear perfluorinated segment F with four carbons (n=4) and a linear non-fluorinated hydrocarbon segment with five carbons (m=5). Furthermore, F6H8 may be used to denote 1-perfluorohexyl-octane or $CF_3(CF_2)_5$—$(CH_2)_7CH_3$ (which may be also, alternatively expressed as formula $F(CF_2)_6(CH_2)_8H$), which has a linear perfluorinated segment F with six carbons (n=6) and a linear non-fluorinated hydrocarbon segment with 8 carbons (m=8).

The pharmaceutical composition of the invention comprising of "a" semifluorinated alkane is to be understood herein, as comprising at least one semifluorinated alkane of Formula (II) as described above. Optionally, however, the composition may comprise of more than one, for example, a mixture of two or more semifluorinated alkanes of Formula (II), i.e. of any one of the semifluorinated alkane species as described above.

In a preferred embodiment, the pharmaceutical composition according to the present invention comprises a semifluorinated alkane of Formula (II) which is selected from 1-perfluorohexyl-octane ($CF_3(CF_2)_5$—$(CH_2)_7CH_3$ (F6H88)) and 1-perfluorobutyl-pentane ($CF_3(CF_2)_3$—$(CH_2)_4CH_3$ (F4H55)). In a particular preferred embodiment of the present invention, the semifluorinated alkane of Formula (II) is 1-perfluorohexyl-octane ($CF_3(CF_2)_5(CH_2)_7CH_3$, F6H88).

In yet a further embodiment, the liquid vehicle of the pharmaceutical composition of the present invention may consist of a semifluorinated alkane of Formula (II) as specified above. In this context also, the term "a" semifluorinated alkane is to be understood as at least one semifluorinated alkane, but may also include the option of more than one, or a plurality of semifluorinated alkane compounds. Accordingly, in one embodiment, the composition may consist of more than one semifluorinated alkane of Formula (II) as specified above.

In another embodiment, the pharmaceutical composition according to the present invention may comprise (a) timolol and/or a pharmaceutically acceptable salt thereof, and (b) a liquid vehicle comprising or essentially consisting of a semifluorinated alkane of general formula (II) as defined above, or a semifluorinated alkane selected from any one, or combination of the semifluorinated alkane compounds as defined above, and optionally, (c) one or more excipients.

As used herein, the term "consists" and related terms "consisting" or "consist" is to be understood as meaning that no other features, other than those prefaced by the term are present. In the context of compositions, if any other constituent or component is present in the composition other than those prefaced by such term, then it is present only in trace or residual amounts such as to confer no technical advantage or relevance in respect of the object of the invention, such as may be further understood by the term 'essentially" or "substantially" used in conjunction with these terms (e.g. 'essentially consisting of"). It is to be understood that isomeric or olefinic impurities that originate from synthesis of semifluorinated alkanes and that are present in only trace or residual amounts, as these cannot be quantitatively removed upon purification, and that do not confer any technical advantage or relevance in respect of the object of the present invention, do fall under the above definition of such other constituent or component. In contrast, the term ‘comprising” or related terms “comprises” or “comprise” in the context of the present compositions, is to be understood as meaning that other features, other than those prefaced by the term may be present in the composition.

In a further embodiment, the liquid vehicle of the present pharmaceutical composition as defined in any of the previous embodiments described above, preferably comprises a semifluorinated alkane or optionally, a mixture of semifluorinated alkanes in an amount of at least 70% (w/w), 75% (w/w), 85% (w/w), 90% (w/w), 95% (w/w), 98% (w/w), 98.5% (w/w), 99% (w/w), 99.5% (w/w), 99.8% (w/w) or at least 99.9% (w/w) of a semifluorinated alkane or a mixture of semifluorinated alkanes as described above, with respect to the total weight of the liquid vehicle. In a preferred embodiment, the liquid vehicle of the present pharmaceutical composition comprises a semifluorinated alkane in an amount of at least 98% w/w.

In a further embodiment, the liquid vehicle of the present invention essentially consists of 100% (w/w) of a semifluorinated alkane or mixture of semifluorinated alkanes.

The term “% (w/w)” as used herein and unless indicated otherwise refers to the amount of a component of a composition as a weight percentage in relation to the total weight of the liquid vehicle of the present pharmaceutical composition (with ‘w’ denoting weight).

In a particularly preferred embodiment, the liquid vehicle of the pharmaceutical composition according to the present invention comprises 1-perfluorohexyl-octane ($CF_3(CF_2)_5$—$(CH_2)_7CH_3$ (F6H8)). In a further preferred embodiment, the liquid vehicle of the pharmaceutical composition of the present invention essentially consists of 1-perfluorohexyl-octane (F6H8). It is understood that a liquid vehicle essentially consisting of 1-perfluorohexyl-octane may comprise in trace or residual amounts isomeric or olefinic impurities (such as 2-perfluorohexyl-octane or 1-perfluorohexyl-octene) originating from synthesis of F6H8 which cannot be quantitatively removed upon purification.

In further preferred embodiments, the liquid vehicle of the pharmaceutical composition according to the present invention comprises 1-perfluorobutyl-pentane ($CF_3(CF_2)_3$—$(CH_2)_4CH_3$ (F4H5)). In a further preferred embodiment, the liquid vehicle of the pharmaceutical composition of the present invention essentially consists of 1-perfluorobutyl-pentane (F4H5). It is understood that a liquid vehicle essentially consisting of 1-perfluorobutyl-butane may comprise in trace or residual amounts isomeric or olefinic impurities (such as 2-perfluorobutyl-pentane or 1-perfluorobutyl-pentene) originating from synthesis of F4H5 which cannot be quantitatively removed upon purification.

The liquid semifluorinated alkanes as described above are chemically and physiologically inert, colourless and stable. Their typical densities range from 1.1 to 1.7 g/cm$^3$, and their surface tension may be as low as 19 mN/m. Semifluorinated alkanes of the RFRH type are insoluble in water but also somewhat amphiphilic, with increasing lipophilicity correlating with an increasing size of the non-fluorinated segment.

The liquid vehicle of the pharmaceutical composition comprising a semifluorinated alkane as described above may also comprise a further solubilizing agent, such as one or more solvents or co-solvents. In specific embodiments, the liquid vehicle of the present pharmaceutical composition may comprise a co-solvent, preferably an organic co-solvent.

As used herein, the term “solubilizing agent” may denote a compound or solvent or a co-solvent, preferably an organic solvent, that is miscible with the semifluorinated alkane or the mixture of different semifluorinated alkanes of the present liquid vehicle and that enhances or facilitates the solubility, or the dispersability of the active component timolol in the chosen liquid vehicle comprising a semifluorinated alkane as described above.

Examples of potentially useful organic co-solvents include glycerol, propylene glycol, polyethylene glycol, and ethanol. However, the concentration of the co-solvent should preferably be low relative to that of the semifluorinated alkane or semifluorinated alkane mixture. The co-solvent comprised in the liquid vehicle of the pharmaceutically composition according to the invention may be ethanol. If an organic co-solvent such as ethanol is used, it is recommendable to keep it at or below a level of approximately 10% (w/w) or 5% (w/w) or even 3% (w/w) with regard to the total weight of the liquid vehicle. Preferably, the content of ethanol is from about 0.1 to about 2% (w/w), and more preferably not more than about 1% (w/w) with regard to the total weight of the liquid vehicle. In some embodiments, the liquid vehicle of the present composition according to the invention, however, are free of an organic co-solvent.

In other embodiments, the solubilizing agent, that may be optionally comprised by the liquid vehicle of the present pharmaceutical composition, may preferably be present in an amount of up to 3% (w/w), or preferably of up to 2.5% (w/w) with respect to the total weight of the liquid vehicle. In a preferred embodiment, the liquid vehicle comprises a solubilising agent in amounts as low as up to 1% (w/w), preferably up to 0.5% (w/w) with respect to the total weight of the liquid vehicle. In another preferred embodiment, the liquid vehicle further comprises a solubilising agent in an amount of from about 2.5% to 0.5% (w/w), preferably of from about 1% to 0.5% (w/w) with respect to the weight of the liquid vehicle.

In some embodiments, the solubilizing agent may be a liquid excipient such as, for example, a further organic co-solvent as described above and/or an oil selected from glyceride oils, liquid waxes and liquid paraffin, or an organic solvent exhibiting a high degree of biocompatibility.

Examples of potentially useful liquid excipients comprise oily excipients which may be used in combination with one or more semifluorinated alkanes and include triglyceride oils, mineral oil, medium chain triglycerides (MCT), oily fatty acids isopropyl myristate, oily fatty alcohols, esters of sorbitol and fatty acids, oily sucrose esters or any other substance which is physiologically tolerated by the eye. In one of the preferred embodiment, the liquid vehicle comprises a solubilizing agent in form of a liquid excipient. Further examples of potentially useful solubilizing agents as used herein are organic solvents. Preferred organic solvents include glycerol, propylene glycol, polyethylene glycol and ethanol. In yet further preferred embodiments, the liquid vehicle of the present pharmaceutical composition may comprise ethanol as the solubilizing agent, preferably in an amount of up to 1% (w/w), more preferably of up to 0.8% (w/w) and most preferred of up to 0.5% (w/w) with regard to the total weight of the liquid vehicle of the present pharmaceutical composition.

The pharmaceutical composition of the present invention comprises, as a constituent a), the active ingredient timolol and/or a pharmaceutically acceptable salt thereof, preferably timolol maleate, as described above. The present pharmaceutical composition may comprise timolol and/or a pharmaceutically acceptable salt thereof in an amount of from about 0.1% (w/v) to about 10% (w/v), or from about 0.1% (w/v) to about 5% (w/v), or from about 0.2% (w/v) to about 3% (w/v), or from about 0.2% (w/v) to about 2% (w/v), or from about 0.5% (w/v) to about 2% (w/v), or from about 0.5% (w/v) to about 1.5% (w/v).

In preferred embodiments, the present pharmaceutical composition comprises timolol and/or a pharmaceutically acceptable salt thereof, preferably timolol maleate or (S)-timolol hemihydrate, most preferably timolol maleate, in a concentration corresponding to a concentration of timolol free base of from about 0.5% (w/v) to about 2.0% (w/v), preferably from about 0.5% (w/v) to about 1.5% (w/v).

In a preferred embodiment, the pharmaceutical composition of the present invention comprises a) timolol maleate, preferably at a concentration of from about 0.4 to 3.4% (w/v), more preferably of from about 0.6 to about 3% (w/v), even more preferably of from about 0.68 to about 2.7% (w/v), most preferably at a concentration of from about 0.68% to about 2.1% (w/v).

Unless otherwise indicated, the term "% (w/v)" as used throughout herein in connection with the present pharmaceutical composition denotes the amount of a component of a composition as a weight percentage in relation to the total volume of the composition (with 'w' denoting the weight and 'v' denoting volume). For example, 0.05% (w/v) may be understood as relating to 0.5 mg of a component in 1 mL of the composition, and 0.1% (w/v) would correspond to 1.0 mg of a component in 1 mL of the composition.

The active component timolol and/or a pharmaceutically acceptable salt thereof, preferably timolol maleate or (S)-timolol hemihydrate, more preferably timolol maleate as described above, may be dissolved, dispersed or suspended in the liquid vehicle comprising a semifluorinated alkane as described below. Accordingly, the liquid pharmaceutical composition of the present invention may be in the form of a solution, preferably a clear solution or in form of a suspension.

In preferred embodiments, the pharmaceutical composition of the present invention is provided in form of a suspension. A suspension may be defined as a type of a dispersion, a dispersion being a system having at least one continuous (or coherent) phase and at least one discontinuous (or inner) phase which is dispersed in the continuous phase. In a suspension, the dispersed phase is in the solid state. Preferably, the suspensions useful for practising the present invention are liquids, at least at physiological temperature, which means that the continuous phase is a liquid. Typically, the suspensions are also liquid at room temperature.

Preferably, the present invention provides a pharmaceutical composition in which particles of timolol and/or a pharmaceutically acceptable salt thereof, preferably timolol maleate or (S)-timolol hemihydrate, more preferably timolol maleate, as the dispersed phase are suspended in a liquid vehicle comprising a semifluorinated alkane, for example, a semifluorinated alkane of formula (II) as defined above as the continuous phase. Accordingly, in preferred embodiments of the present invention, the timolol and/or a pharmaceutically acceptable salt thereof is suspended in the liquid vehicle comprising a semifluorinated alkane.

In further preferred embodiment, the particles of timolol and/or a pharmaceutically acceptable salt thereof, preferably of timolol maleate or (S)-timolol hemihydrate, more preferably timolol maleate, are solid particles.

In further preferred embodiments, the pharmaceutical composition of the present invention comprises timolol and/or a pharmaceutically acceptable salt thereof suspended in the liquid vehicle b), at a concentration corresponding to a concentration of timolol free base of from 0.3 to 2.5% (w/v), preferably of from 0.5 to 2.0% (w/v), more preferably of from about 0.5 to 1.5% (w/v). For example, considering that 1.3668 mg timolol maleate correspond to 1.0 mg timolol free base, in a preferred embodiment of the present invention, component a) is timolol maleate suspended at a concentration of from about 0.4 to about 3.4% (w/v), preferably of from about 0.6 to about 3% (w/v), more preferably of from about 0.68 to about 2.7% (w/v), most preferably at a concentration of from about 0.68% to about 2.1% (w/v).

The particle size of the timolol and/or pharmaceutically acceptable salt thereof is preferably below about 100 μm, which means that most of the particles, e.g. at least about 90% thereof, have a size below 100 μm. Which type of particle diameter is considered as particle size will depend on the method used for particle size distribution, which in turn is selected to be appropriate for the type of solid material and the approximate size range. For example, laser diffraction or dynamic light scattering (also known as photon correlation spectroscopy or quasi-elastic light scattering) are appropriate methods for determining particle sizes in the colloidal and low micron range, whereas sedimentation analysis, sieve analysis or photoanalysis may be selected for larger particle sizes.

In a further preferred embodiment, at least about 90% of the suspended timolol and/or a pharmaceutically acceptable salt thereof have a particle size of not more than about 20 μm, preferably of not more than about 15 μm. In a most preferred embodiment, at least 90% of the suspended particles of timolol and/or a pharmaceutically acceptable salt thereof have a size lower than about 10 μm, more preferred have size lower than about 5 μm. Especially for ophthalmic administration, at least about 90% of the suspended particles of timolol and/or a pharmaceutically acceptable salt thereof have a size lower than about 20 μm, preferably with at least about 90% of the suspended particles having a size of not more than about 15 μm, more preferably of not more than about 10 μm, most preferably of not more than about 5 μm, as measured by state-of-the-art particle size distribution techniques (e.g. laser diffraction, dynamic light scattering).

The pharmaceutical composition comprising timolol and/or a pharmaceutically acceptable salt thereof, preferably timolol maleate, especially when suspended in a liquid vehicle comprising a semifluorinated alkane, displays advantageous stability, especially with regard to the size of the suspended particles. As known from other pharmaceutical compositions in form of suspensions, the suspended particles may aggregate, and depending on the forces by which the particles attract each other, the aggregates thus formed may be rather difficult to resuspend. A further problem associated with that is that in suspensions having non-uniform particle sizes there is a tendency for smaller particles to gradually dissolve, whereas larger particles grow through the deposition of dissolved material onto their surfaces (Ostwald ripening). In result, the particle size distribution of a suspension may become broader over time. Particles which grow beyond a certain size may be unsuitable for the intended use; for example, they may occlude an injection cannula or, in case of ophthalmic administration, irritate or even damage the ocular surface.

In contrast to this, it was found that the pharmaceutical composition of the present invention comprising timolol and/or a pharmaceutically acceptable salt thereof, especially when provided in form of a suspension, can be stored for prolonged periods of time without significantly changing their particle size distribution. Accordingly, the pharmaceutical composition of the present invention comprising timolol and/or a pharmaceutically acceptable salt thereof, preferably timolol maleate or (S)-timolol base hemihydrate, more preferably timolol maleate, in form of a suspension may be stored for extended periods of time, such as, for example for up to 1 year, or up to 6 months, or up to 3 months, or up to 2 months or up to 1 month without significantly changing their particle size distribution of the suspended particles. In exemplary embodiments, the present invention provides a pharmaceutical composition comprising timolol and/or a pharmaceutically acceptable salt thereof in form of a suspension, wherein at least about 90% of the suspended particles of timolol and/or a pharmaceutically acceptable salt thereof have a size of not more than about 15 μm, after three weeks of storage at room temperature. The term room temperature as used herein is to be understood throughout as a temperature in the range of 20 to 25° C.

In another exemplary embodiment, the present invention provides a pharmaceutical composition comprising timolol and/or a pharmaceutically acceptable salt thereof in form of a suspension, wherein at least about 90% of the suspended particles of timolol and/or a pharmaceutically acceptable salt thereof have a size of not more than about 10 μm, after three weeks of storage at room temperature.

In contrast to some other suspensions known in prior art, the pharmaceutical composition of the present invention when present in the form of a suspension usually requires no surfactant, or, if at all, only small amounts of surfactant, for its physical stabilisation. This is a significant advantage as surfactants have a substantial potential for irritation and local toxicity, especially when administered to the eye or by injection. According to one of the preferred embodiments, the pharmaceutical composition of the invention is substantially free of surfactant. In a further preferred embodiment, the total amount of surfactant or surfactants, if more than one surfactant is incorporated, is not more than about 5% (w/w), in particular not more than about 3% (w/w), or preferably not more than about 1% (w/w), respectively, with regard to the total weight of the final composition. In further preferred embodiments, the amount is not more than about 0.5% (w/w), or not more than about 0.25% (w/w), respectively.

In this context, the semifluorinated alkanes as described herein, although they possess some amphiphilic properties due to their chemical structure which includes fluorinated and non-fluorinated alkyl (or alkylene) groups characterised by different degrees of lipophilicity, are not understood as being within the scope of surfactants.

The surfactants which may be absent or only present in small amounts include non-ionic, cationic, anionic, and zwitterionic surfactants as commonly used as excipients in various types of pharmaceutical compositions, e.g. as wetting agents, emulsifiers, dispersing agents, solubilisers and the like. Examples of surfactants which may be considered potentially useful include tyloxapol, poloxamers such as Pluronic F68LF or Lutrol F68, Pluronic L-G2LF and Pluronic L62D, polysorbates such as polysorbate 20 and polysorbate 80, polyoxyethylene castor oil derivatives, sorbitan esters, polyoxyl stearates, lecithins, purified or synthetic phospholipids, and mixtures of two or more thereof.

The pharmaceutical composition of the invention may further comprise excipients in range of up to about 10% (w/v), more preferably up to about 5% (w/v), even more preferably up to about 2% (w/v) such as, for example, non-fluorinated organic liquids, for example in order to modify the properties of the liquid vehicle, such as the viscosity. Such other liquid may be an oil selected from glyceride oils, liquid waxes, and liquid paraffin, or an organic solvent exhibiting a high degree of biocompatibility, or a mixture of more than one liquid excipients.

Examples of potentially useful oily excipients which may be used in combination with one or more semifluorinated alkanes as described above may include triglyceride oils (i.e. soybean oil, olive oil, sesame oil, cotton seed oil, castor oil, sweet almond oil), mineral oil (i.e. petrolatum and liquid paraffin), medium chain triglycerides (MCT), oily fatty acids, isopropyl myristate, oily fatty alcohols, esters of sorbitol and fatty acids, oily sucrose esters, or any other oily substance which is physiologically tolerated by the eye.

The composition of the present invention may, of course, comprise further pharmaceutical excipients as required or useful. Potentially useful excipients include acids, bases, antioxidants, stabilisers, synergists, colouring agents and thickening agents. In a preferred embodiment, however, the liquid vehicle of the pharmaceutical composition according to the present invention is free of any excipients.

Furthermore, the invention provides a means of formulating pharmaceutical compositions, preferably ophthalmic pharmaceutical compositions comprising timolol and/or a pharmaceutically acceptable salt thereof, preferably timolol maleate, which are microbiologically stable. This is due to the fact that semifluorinated alkanes as comprised by the liquid vehicle of the present compositions and as described above are not normally prone to microbial contamination. Hence, it is possible to formulate preservative-free ophthalmic compositions which are better tolerable for many patients, in particular patients suffering from an ophthalmic disease or condition. The preservative-free ophthalmic composition may be provided both in multi-dose or single-dose format.

Accordingly, although the pharmaceutical composition of the present invention may comprise a pharmaceutically acceptable preservative, in a preferred embodiment, the pharmaceutical composition of the present invention is free of a preservative. This is especially useful when the composition of the present invention is provided not only in dosage forms for single use (single dosage forms), but especially in multiple dosage forms with a plurality of doses.

In a further embodiment, water may also be present in the pharmaceutical composition of the present invention, however, preferably in small amounts of up 1.0% (w/w) or even of only up to 0.1% (w/w) or less, based on the final composition (final dosage form). In a preferred embodiment, the pharmaceutical composition, preferably the liquid vehicle of the pharmaceutical composition of the present invention is essentially free of water, whereas the residual water may be attributed to the potential residual water content of the active ingredient timolol and/or a pharmaceutically acceptable salt thereof, especially timolol maleate. The term 'essentially' as used herein means if present then in trace or residual amounts such as to confer no technical advantage or relevance in respect of the object of the invention.

For example, 1-perfluorohexyl-octane (F6H8) or 1-perfluorobutyl-pentane (F4H5) as preferred semifluorinated alkanes in some embodiments of the present invention do not comprise any water, or have a water content of no more than the maximal solubility of water in 1-perfluorohexyl-octane or in 1-perfluorobutyl-pentane; for example 1-perfluorobutyl-pentane has a water-content of less than $1.6\times10^{-4}$ mg/ml as determined by methods known in the art for moisture analysis, such as Karl-Fischer titration methods.

In preferred embodiments, the pharmaceutical composition of the present invention essentially consists of timolol maleate and a semifluorinated alkane selected from 1-perfluorobutyl-pentane (F4H5) and 1-perfluorohexyl-octane (F6H8). In further embodiments, the pharmaceutical composition of the present invention essentially consists of timolol maleate and 1-perfluorohexyl-octane (F6H8), more specifically of timolol maleate suspended in 1-perfluorohexyl-octane (F6H8).

In exemplary embodiments, the pharmaceutical composition of the present invention consists of from about 90 to about 99.99% (w/w), more preferably from about 95 to about 99.9% (w/w), more preferably from 97 to 99% (w/w) even more preferably from 98 to 99% (w/w) of the liquid vehicle comprising a semifluorinated alkane as described above, preferably a semifluorinated alkane selected from F4H5 and F6H8, based on the weight of the final composition.

Liquid suspensions may be prepared by conventional methods. The solid timolol and/or pharmaceutically acceptable salt thereof, preferably timolol maleate or (S)-timolol-hemihydrate, more preferably timolol maleate, may be suspended in the liquid vehicle comprising the semifluorinated alkane. Alternatively, the particles of timolol and/or pharmaceutically acceptable salt thereof, preferably timolol maleate or (S)-timolol-hemihydrate, more preferably timolol maleate, may be precipitated in situ by adding a—typically organic—solution of the active ingredient (and, optionally, one or more solid excipients) under controlled conditions to the semifluorinated alkane-based vehicle.

Conventional grinding or milling methods using standard equipment such as a ball mill, hammer mill, roller mill, colloidal mill, jet mill, or the like may be used. If the particle size is to be reduced after preparation of a suspension, ultrasonication as well as various types of homogenisers may be used, such as colloid mills or high-pressure homogenisers.

In a preferred embodiment, the particle sizes of timolol and/or pharmaceutically acceptable salt thereof, preferably timolol maleate or (S)-timolol-hemihydrate, more preferably timolol maleate, when provided in form of a liquid suspension, are adjusted by first combining the drug particles with a liquid vehicle comprising or consisting of a semifluorinated alkane such as described in any one of the above embodiments, followed by a step of milling or grinding according to any of the above methods.

The pharmaceutical composition in suspended form in a liquid vehicle comprising a semifluorinated alkane provides several advantageous properties over conventional, aqueous or not semifluorinated alkane-based formulations, especially with respect to topical administration for ophthalmic use. For example, when conventional perfluorinated compounds are used as liquid vehicles, the suspensions tend to separate very rapidly by flotation of the dispersed phase, or by its sedimentation, depending on the relative densities of the dispersed phase and of the continuous phase. This is accompanied by a rapid formation of particle aggregates which may be dense and poorly re-dispersible. Rapid flotation or sedimentation makes precise and reproducible dosing very challenging, if not impossible. For example, if an ophthalmic suspension settles very rapidly after shaking, the first dosing from a full container, if not withdrawn immediately upon shaking, will contain a lower-than-intended number of drug particles, unless the container is held upside down, in which case more than the intended quantity of drug particles will be dispensed. When the same container is nearly empty and the last doses are dispensed, the drug dose withdrawn per volume will be too high if it was low in the beginning, and vice versa.

Moreover, aggregates may easily obstruct the dispensing channels or openings of containers and thereby lead to erroneous dosing. If dispensed from the container, they may cause irritation of the conjunctiva or of the cornea, depending on their size, shape and hardness.

In contrast, the semifluorinated alkane-based suspensions comprising timolol and/or a pharmaceutically acceptable salt thereof according to some embodiments of the invention remain finely dispersed and homogeneous. If flotation or sedimentation takes place, it occurs slowly, leaving sufficient time for the patient to withdraw a dose after shaking the container. The formation of large aggregates is not observed. After flotation or sedimentation, the drug particles are easily re-dispersed by gentle shaking, and appear to largely retain their original particle size distribution. Preferably, the pharmaceutical composition of the present invention is a suspension, wherein the particles of timolol and/or a pharmaceutically acceptable salt, preferably timolol maleate, are re-dispersible, for example by gentle shaking.

These properties of semifluorinated alkane-based suspensions of timolol and/or pharmaceutically acceptable salt thereof result in superior pharmaceutical quality and performance characteristics for the use of timolol in for example the treatment of ocular diseases. The level of convenience to the patient and/or health care provider is greatly increased. More importantly, the dosing accuracy, i.e. precision and reproducibility of dosing, is greatly improved over other types of pharmaceutical suspensions. This will bring about a more reliable therapeutic effect and a reduced risk of adverse effects which result from overdosing.

A further surprising advantage of the presently described—compositions in form of suspensions of timolol or and/or a pharmaceutically acceptable salt thereof suspended in a semifluorinated alkane is that they appear to form very small droplets when dispensed from a dropper such as an eye dropper. Without wishing to be bound by theory, it is believed that the small droplet size is a result of an interplay of the semifluorinated alkane's unique properties in terms of their density, viscosity, and surface tension. In any case, it is believed that for topical administration into an eye a small drop or volume of administration is highly advantageous as the capability of the lacrimal sac to accept and hold fluid is extremely limited. In fact, it is very common that the administration of a conventional eye drop formulation based on water or oil immediately leads to a discharge of a substantial fraction of the administered medicine as well as some tear fluid. At the same time, there is a risk that some of the administered dose will be taken up systemically via the nasolacrimal duct. Hence, if an effective dose of an active ingredient can be incorporated in a small volume of liquid which can be dispensed as a very small droplet, this should also contribute to a substantially increased dosing reliability and reproducibility, thus enhancing the safety and effectiveness of the therapy.

A yet further advantage of the invention which is based on the use of semifluorinated alkanes is that they can be designed or mixed for an optimally adjusted evaporation behaviour after administration. Thus, it is possible to formulate for example an ophthalmic composition which delivers timolol or a salt thereof efficiently to the eye in such a way that the liquid vehicles is subsequently eliminated via evaporation. This is in sharp contrast to oily or perfluorinated eye drop vehicles which do easily not evaporate and thus form non-physiological residues at the site of administration, e.g. in the lacrimal sac.

In a second aspect, the present invention provides the pharmaceutical composition according to the first aspect of the invention, namely pharmaceutical composition comprising:

(a) timolol and/or a pharmaceutically acceptable salt thereof, and (b) a liquid vehicle comprising a semifluorinated alkane for use as a medicament.

The pharmaceutical composition including all embodiments thereof as described above for the first aspect of the invention is especially useful for the therapy or prevention of diseases or conditions or any symptoms associated therewith related to an eye of a subject, preferably to an eye of a human subject.

The pharmaceutical composition of the present invention may be especially useful as an ophthalmic composition and may be administered to the eye of a subject. More specifically, the pharmaceutical composition of the present invention may be administered topically to the eye of a subject, for example to the eye lid, eye sac, eye surface and/or to an ophthalmic tissue of a patient. Preferably, the pharmaceutical composition of the present invention may be topically administered to an outer surface of an eye of a patient or to an ophthalmic tissue which is readily accessible by the patient or by another person administering the pharmaceutical composition to the eye of the patient in need thereof.

The present pharmaceutical composition, especially when used as liquid of either low or higher viscosity (usually in the range of 1 to 3.5 mPa s) may advantageously be administered in form of drops or by spraying or by injection. Most preferably, however, the liquid pharmaceutical composition of the present invention, especially when provided in the form of a suspension, may be administered as drops, more specifically as eyedrops to be administered topically to the eye.

Depending on the extent of the disease, or whether or not both eyes of the patient to be treated are affected, the drops or eyedrops of the present ophthalmic pharmaceutical composition may be administered to only one eye or to both eyes of the patient. The present pharmaceutical composition may provide droplet sizes when administered from conventional droppers, with a volume usually in the range from about 5 to about 15 µl. This small droplet size usually facilitates the dropwise administration and, moreover, facilitates precise dosage of the pharmaceutical composition of the present invention. Accordingly, the pharmaceutical composition of the present invention may be administered as single drops with a volume of about 5 to 15 µl per dose per eye, preferably with a volume of about 8 to 15 µl per dose per eye, more preferably with a volume of about 9 to 12 µl per dose per eye, even more preferably with a volume of about 10 to 12 µl per dose per eye and most preferably with a volume of about 11 µl per dose per eye.

Depending on the need, the composition according to the present invention may be administered once (qd), twice (bid), three-times (tid) or four-times (qid) per day per eye. Preferably, the composition according to the present invention is administered up to two-times per day per eye. In a preferred embodiment, the composition of the present invention is administered twice (bid) daily. In a more preferred embodiment, the composition of the present invention is administered once (qd) daily.

The pharmaceutical composition according to the present invention is especially useful in the treatment of glaucoma, increased intraocular pressure (IOP), ocular hypertension and/or a symptom associated therewith.

The present invention provides stable liquid pharmaceutical compositions, especially stable liquid suspensions comprising timolol and/or a pharmaceutically acceptable salt thereof. These compositions can be topically administered and allow the administration of the active ingredient timolol in lower dosages compared to known liquid formulations, thereby reducing the side effects associated to the active ingredient and the additional components of said known liquid formulations, in particular in the treatment of glaucoma.

Based on this, the pharmaceutical composition for the use of the present invention allows for a significant reduction of droplet size and target dose volume as described above associated therewith and therefore, as outlined above, for a significant reduction of the total daily dose of timolol administered for use in the treatment of glaucoma, increased intraocular pressure, ocular hypertension and/or a symptom associated therewith. Accordingly, in a preferred embodiment the present pharmaceutical composition for use in the treatment of glaucoma, increased intraocular pressure (IOP), ocular hypertension and/or a symptom associated therewith, comprises timolol and/or a pharmaceutically acceptable salt thereof, preferably timolol maleate, suspended in the liquid vehicle comprising a semifluorinated alkane at a concentration corresponding to a concentration of timolol free base of from 0.3 to 2.5% (w/v), preferably at a concentration of from 0.5 to 2.0% (w/v), more preferably of from about 0.5 to 1.5% (w/v). In said preferred embodiments, the liquid vehicle comprises or essentially consists of a semifluorinated alkane, as defined by Formula (II) or any one of the semifluorinated alkanes as defined above, such as a semifluorinated alkane selected from 1-perfluorobutyl pentane or 1-perfluorohexyl octane. In further embodiments, the pharmaceutical composition for the use according to the present invention may be administered in a dose volume per eye of 10 to 12 µl wherein the timolol and/or a pharmaceutically acceptable salt thereof may be suspended in the liquid vehicle in a concentration of at least 0.3% (w/v), preferably of at least 0.5% (w/v).

In a preferred embodiment of the present invention, the single dose of timolol as free base administered per eye is from about 33 to about 280 µg, preferably of from about 55 to about 220 µg, more preferably of from about 55 to about 165 µg, most preferably of from about 55 to about 150 µg. In a more preferred embodiment, the pharmaceutical composition for use in the treatment of glaucoma, increased intraocular pressure (IOP), ocular hypertension and/or a symptom associated therewith comprises a) timolol maleate suspended in a semifluorinated alkane, preferably F6H8, wherein the dose of timolol, as a free base, administered per eye is from about 55 to about 165 µg, more preferably from about 55 to about 150 µg.

In another embodiment, the pharmaceutical composition for use in the treatment of glaucoma, increased intraocular pressure (IOP), ocular hypertension and/or a symptom associated therewith, may be administered to subjects concomitantly suffering from dry eye disease and/or hypertension and/or cardiac related diseases. Thus, the pharmaceutical composition for use in the treatment of glaucoma, increased intraocular pressure (IOP), ocular hypertension and/or a symptom associated therewith, is effective in not exacerbating comorbidities such as dry eye disease and/or hypertension and/or cardiac related diseases.

In another preferred embodiment, the pharmaceutical composition for use in the treatment of glaucoma, increased intraocular pressure (IOP), ocular hypertension and/or a symptom associated therewith is effective in reducing side effects derived from the treatment of glaucoma or ocular hypertension with non-selective beta blockers at higher dosages, wherein said side effects are exacerbation of chronic obstructive airways disease and/or bronchospasm and/or dry eye symptoms.

In a third aspect, the present invention provides a method for the treatment of glaucoma, increased intraocular pressure, ocular hypertension and/or a symptom associated therewith, comprising administering to the eye of a subject in need thereof a pharmaceutical composition according to the first aspect of the invention, namely a pharmaceutical composition comprising:

(a) timolol and/or a pharmaceutically acceptable salt thereof, and (b) a liquid vehicle comprising a semifluorinated alkane.

Accordingly, the method according to this aspect of the present invention comprises:

providing a composition comprising:

(a) timolol and/or a pharmaceutically acceptable salt thereof, and (b) a liquid vehicle comprising a semifluorinated alkane, and topically administering said composition to a surface of the eye of the subject, or the patient.

It should be noted that for the method according to this aspect of the invention all embodiments and preferred embodiments as described above in connection with the other aspects of the invention apply respectively. The subject, or patient in one embodiment may be a human. In another embodiment, the subject may be a veterinary subject or patient.

In yet a further aspect, the present invention provides for the use of the pharmaceutical composition according to the first aspect of the invention, namely a pharmaceutical composition comprising:

(a) timolol and/or a pharmaceutically acceptable salt thereof, and (b) a liquid vehicle comprising a semifluorinated alkane for the manufacture of a medicament for the treatment of glaucoma, increased intraocular pressure, ocular hypertension and/or a symptom associated therewith. It should be noted that for the manufacture of a medicament according to this aspect of the invention, all embodiments and preferred embodiments as described above in connection with the other aspects of the invention apply respectively.

In yet a further aspect, the present invention provides a pharmaceutical kit comprising the composition as described above in connection with any aspect of the invention, namely a pharmaceutical composition comprising:

(a) timolol and/or a pharmaceutically acceptable salt thereof, and (b) a liquid vehicle comprising a semifluorinated alkane, and a container adapted for holding the pharmaceutical composition. Preferably, the container which contains the pharmaceutical composition of the present invention further comprises a drop dispenser or device adapted for administering the pharmaceutical composition.

In specific embodiments of the kit according to this aspect of the present invention, the container has a dispensing means such as a dropping device adapted for topically administering the composition to the eye of a subject or patient, more specifically dispensing means for dropwise topical administration to a surface of the eye of a subject or patient. In one of the preferred embodiments, the dispensing means is adapted to dispense the pharmaceutical composition dropwise in volumes of less than about 15 µl per drop. In further embodiments, the dispensing means is adapted to dispense drops having a volume of less than about 13 µl, 12 µl, or 11 µl, respectively. In particular, drop volumes of less than 12 µl are presently considered very useful in view of the limited holding capacity of one of the preferred sites of administration, the front of the eye. For the avoidance of doubt, such small droplet sizes are primarily enabled by the incorporation of the semifluorinated alkane (or semifluorinated alkanes) according to the invention, and common droppers for eye drops which normally deliver aqueous drops of about 30 to 60 µl are capable of dispensing much smaller drops of semifluorinated alkanes-based formulations.

In the kit according to this aspect of the invention, the container may hold a single dose or a plurality of doses of the present pharmaceutical composition comprising timolol and/or a pharmaceutically acceptable salt thereof and a liquid vehicle comprising a semifluorinated alkane as described above.

Furthermore, the kit according to this aspect of the invention may further comprise instructions for use of the container for dropwise topical administration of the composition to a surface of the eye of a patient. The instructions or directions for use preferably comprised by the kit according to this aspect of the invention may be in any form suited to instruct the user how to perform the topical administration to the affected eye of the patient or subject. It may be in any readable or tangible form, preferably in printed form or in any machine- or computer-readable form preferably in form of a machine-readable optical label such as, for example, a barcode or a QR-code. In a particularly preferred embodiment the directions for use are provided in form of an instruction leaflet, product or package insert or as an enclosed label.

The following are numbered items comprised by the present invention:

1. A pharmaceutical composition comprising:
   (a) timolol and/or a pharmaceutically acceptable salt thereof;
   (b) a liquid vehicle comprising a semifluorinated alkane.
2. The pharmaceutical composition according to item 1, comprising a semifluorinated alkane of the formula (II)

$$CF_3(CF_2)_n(CH_2)_mCH_3 \quad (II),$$

wherein
n is an integer from 3 to 7, and
m is an integer from 4 to 7;
or
wherein
n is an integer from 2 to 10, and
m is an integer from 2 to 10

3. The pharmaceutical composition of item 1 or 2, wherein the semifluorinated alkane is selected from the group consisting of 1-perfluorobutyl-pentane ($CF_3(CF_2)_3(CH_2)_4CH_3$; F4H5), 1-perfluorohexyl-octane ($CF_3(CF_2)_5(CH_2)_7CH_3$, F6H8), 1-perfluorohexyl-hexane ($CF_3(CF_2)_5(CH_2)_5CH_3$, F6H6) and 1-perfluorohexyl-decane ($CF_3(CF_2)_5(CH_2)_9CH_3$, F6H10), preferably one selected from the group consisting of 1-perfluorobutyl-pentane ($CF_3(CF_2)_3(CH_2)_4CH_3$, F4H5), and 1-perfluorohexyl-octane ($CF_3(CF_2)_5(CH_2)_7CH_3$, F6H8).

4. The pharmaceutical composition of any preceding item, wherein the liquid vehicle comprises a co-solvent.
5. The pharmaceutical composition of any preceding item, wherein the liquid vehicle comprises at least 85% (w/w) of a semifluorinated alkane or a mixture of different semifluorinated alkanes.
6. The pharmaceutical composition of any preceding item, wherein the liquid vehicle essentially consists of a semifluorinated alkane or a mixture of different semifluorinated alkanes.
7. The pharmaceutical composition of any preceding item, wherein timolol and/or a pharmaceutically acceptable salt thereof is suspended in the liquid vehicle comprising a semifluorinated alkane.
8. The pharmaceutical composition of any preceding item, wherein component a) is timolol maleate.
9. The pharmaceutical composition of any preceding item, wherein the concentration of timolol free base is from about 0.3 to about 2.5% (w/v).
10. The pharmaceutical composition of any preceding item, wherein component a) is timolol maleate suspended in b) the liquid vehicle.
11. The pharmaceutical composition of any preceding item, wherein the composition is essentially free of water and/or a preservative.
12. The composition of any preceding item, wherein the composition is free of further excipients.
13. The composition of any preceding item, wherein the composition is free of a surfactant.
14. The pharmaceutical composition of any preceding item, comprising timolol in form of timolol maleate and a semifluorinated alkane selected from 1-perfluorobutyl-pentane (F4H5) and 1-perfluorohexyl-octane (F6H8).
15. The pharmaceutical composition of any preceding items, wherein the composition comprises a) timolol in form of timolol maleate and b) 1-perfluorohexyl-octane (F6H8).
16. The pharmaceutical composition of any of item 7 to 15, wherein at least about 90% of the suspended particles of timolol and/or a pharmaceutically acceptable salt thereof have a size of not more than about 15 μm.
17. The pharmaceutical composition of any of item 7 to 16, wherein at least about 90% of the suspended particles of timolol and/or a pharmaceutically acceptable salt thereof have a size of not more than about 15 μm after three weeks of storage at room temperature.
18. The pharmaceutical composition of any preceding item for use as a medicament.
19. The pharmaceutical composition for use according to item 18, for the treatment of glaucoma, increased intraocular pressure, ocular hypertension and/or a symptom associated therewith.
20. The pharmaceutical composition for use according to item 18 or 19, wherein the composition is administered to the eye of a subject.
21. The pharmaceutical composition for use according to any of items 18 to 20, wherein the composition is administered topically to the eye of a subject.
22. The pharmaceutical composition for the use according to any of items 18 to 21, wherein the pharmaceutical composition is administered in a dose volume per eye of from about 8 to about 15 μl, preferably from about 10 to about 12 μl.

23. The pharmaceutical composition for the use according to any of items 18 to 22, wherein the concentration of timolol as free base is of from about 0.3 to about 2.5% (w/v), preferably of from about 0.5 to about 2.0% (w/v), more preferably of from about 0.5 to 1.5% (w/v).
24. The pharmaceutical composition for the use according to any of items 18 to 23, wherein timolol and/or a pharmaceutically acceptable salt thereof is suspended in the liquid vehicle.
25. The pharmaceutical composition for the use according to any of items 18 to 24, wherein the composition is administered up to four times daily, preferably the composition is administered twice daily, more preferably once daily.
26. A method for the treatment of glaucoma, increased intraocular pressure, ocular hypertension and/or a symptom associated therewith, comprising administering to the eye of a subject in need thereof a pharmaceutical composition according to any one of items 1 to 17.
27. The use of a pharmaceutical composition of any of items 1 to 17 for the manufacture of a medicament for the treatment of glaucoma, increased intraocular pressure, ocular hypertension and/or a symptom associated therewith.
28. A kit comprising the pharmaceutical composition according to any one of items 1 to 17 and a container for holding the pharmaceutical composition.
29. The kit according to item 28, wherein the container comprises a drop dispenser for administering the pharmaceutical composition.
30. The kit according to item 29, wherein the container comprises dispensing means for dropwise topical administration to a surface of the eye of a patient, said dispensing means preferably being adapted to dispense the composition dropwise in volumes of less than about 15 μl.
31. The kit according to any of item 28 to 30, wherein the container holds a single dose or a plurality of doses of the composition of any of claims 1 to 17.
32. The kit according to any of items 28 to 31, further comprising instructions for use of the container for dropwise topical administration of the composition to a surface of the eye of a patient.
33. A method of treating glaucoma, increased intraocular pressure, ocular hypertension or a symptom associated therewith, the method comprising administering to an eye of a human with glaucoma, increased intraocular pressure, ocular hypertension or a symptom associated therewith, a composition comprising a) timolol and/or a pharmaceutically acceptable salt thereof and b) a liquid vehicle comprising a semifluorinated alkane, wherein timolol and/or a pharmaceutically acceptable salt thereof is preferably suspended in the liquid vehicle, wherein said method is therapeutically effective in treating glaucoma, increased intraocular pressure, ocular hypertension or a symptom associated therewith.
34. The method according to item 33, wherein component a) is timolol maleate and wherein the concentration of timolol free base is of from about 0.3 to 2.5% (w/v), preferably of from about 0.5 to 2.0% (w/v), more preferably of from about 0.5 to about 1.5% (w/v).

35. The method according to any one of items 33 to 34, wherein the composition target dose volume per eye is from about 10 to about 12 μl, preferably about 11 μl.
36. The method according to any of items 33 to 35, wherein the semifluorinated alkane is selected from F6H8 and F4H5.
37. The method according to item 36, wherein the semifluorinated alkane is F6H8.
38. The method according to any one of items 33 to 37, wherein the composition is administered up to twice daily, preferably once daily.
39. The method according to any one of items 33 to 38, wherein the composition is substantially free of water and of preservative.

DESCRIPTION OF THE DRAWINGS

FIG. 1 is a graphical representation of the results of the measurement of the in-vivo intraocular pressure after administration once a day of a suspension of timolol at a concentration of 0.5% (w/v) in 1-perfluorohexyl-octane (F6H8) versus a formulation of timolol in aqueous solution with a concentration of 0.5% (w/v). The graph shows the chronological progression of the mean intraocular pressure (IOP) as measured in mmHg.

Figure 2:
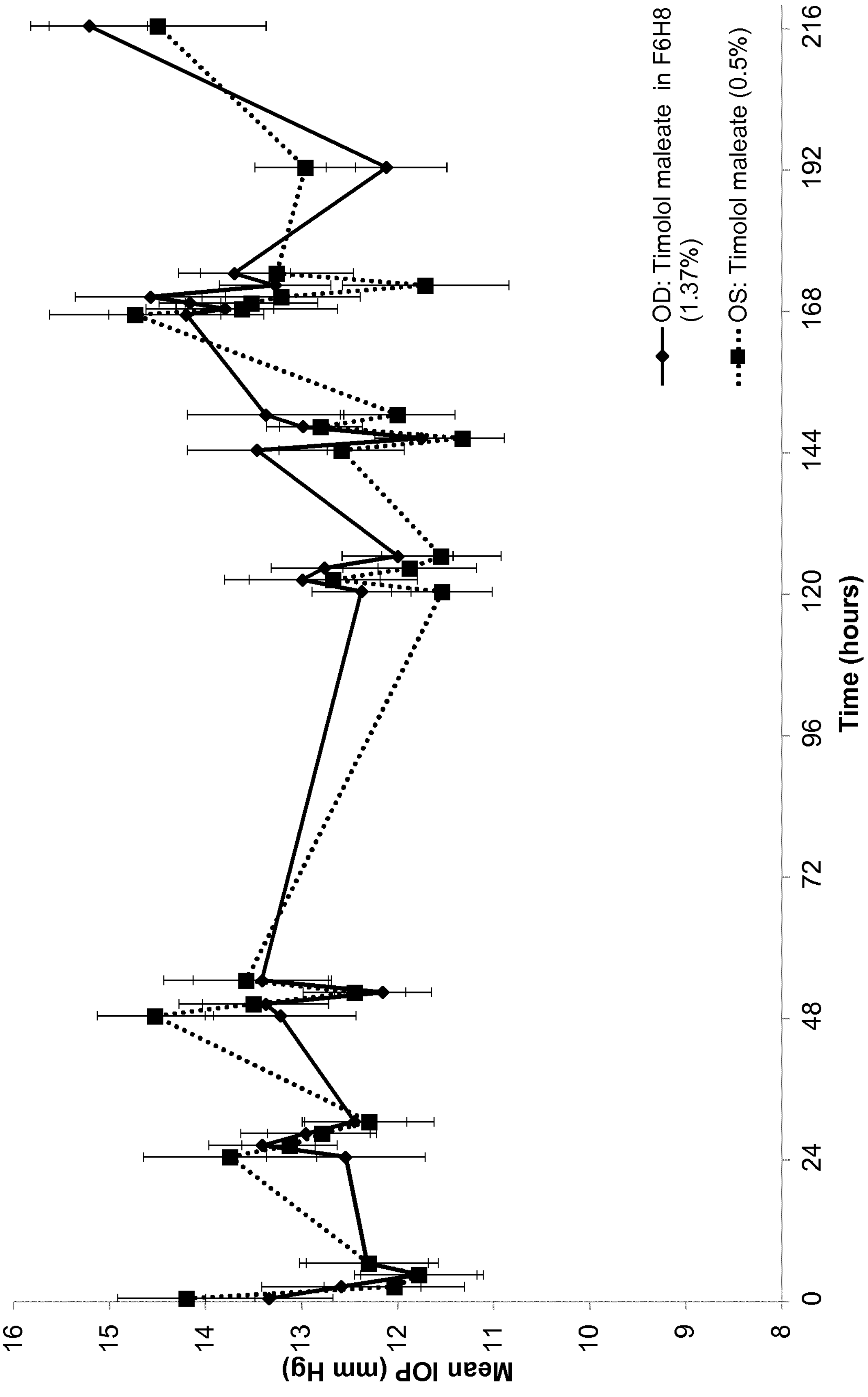
FIG. 2 is a graphical representation of the results of the measurement of the in-vivo intraocular pressure study according to Example 2 below in which a suspension of timolol at a concentration of 1.37% (w/v) in 1-perfluorohexyl-octane (F6H8) is administered once a day.

FIG. 2 is a graphical representation of the results of the measurement of the in-vivo intraocular pressure after administration once a day of a suspension of timolol at a concentration of 1.37% (w/v) in 1-perfluorohexyl-octane (F6H8) versus a formulation of timolol in aqueous solution with a concentration of 0.5% (w/v). The graph shows the chronological progression of the mean intraocular pressure (IOP) as measured in mmHg.

Figure 3:
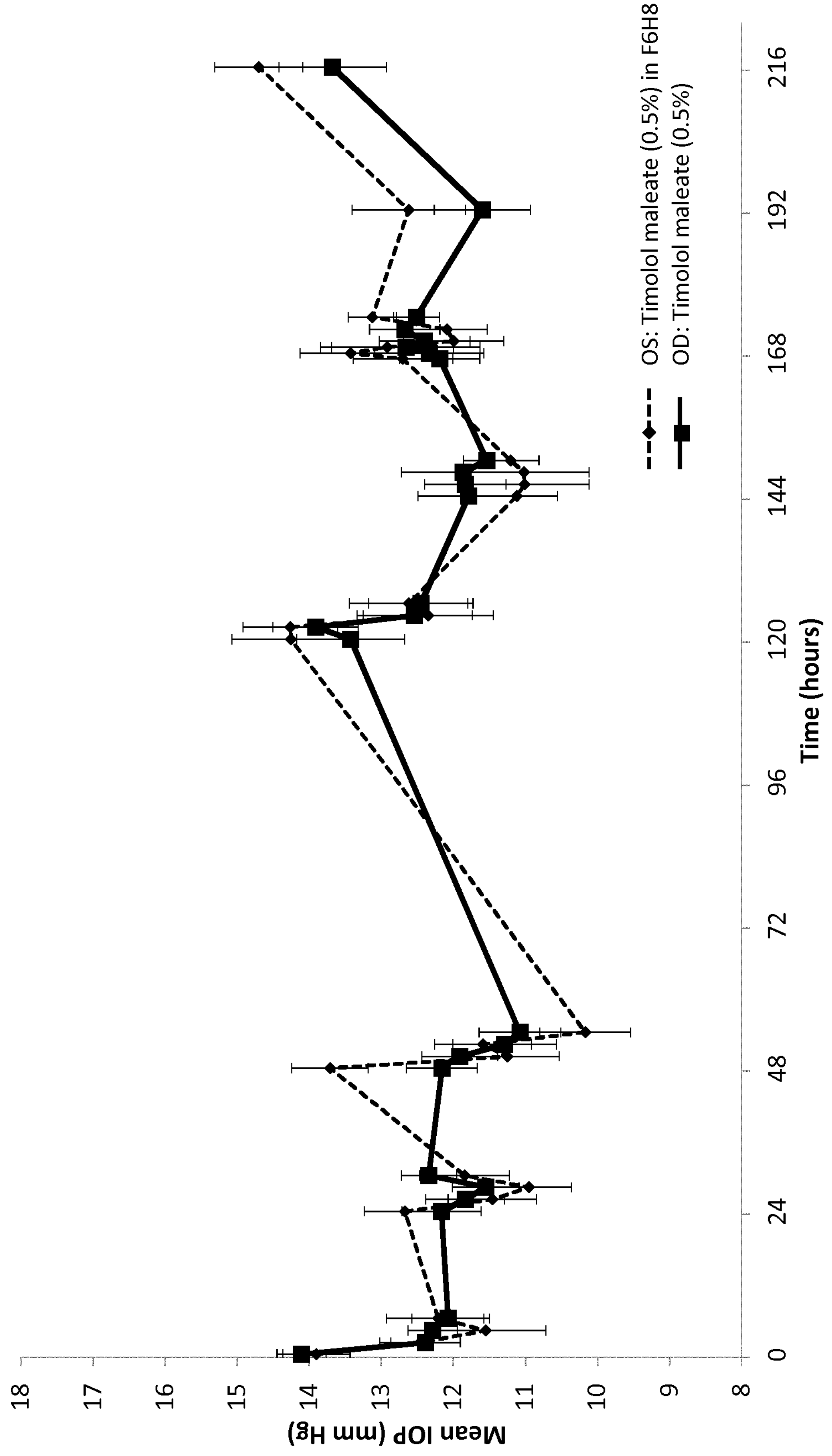
FIG. 3 is a graphical representation of the results of the measurement of the in-vivo intraocular pressure study according to Example 2 below in which a suspension of timolol at a concentration of 0.5% (w/v) in 1-perfluorohexyl-octane (F6H8) is administered twice a day.

FIG. 3 is a graphical representation of the results of the measurement of the in-vivo intraocular pressure after administration twice a day of a suspension of timolol at a concentration of 0.5% (w/v) in 1-perfluorohexyl-octane (F6H8) versus a formulation of timolol in aqueous solution with a concentration of 0.5% (w/v). The graph shows the chronological progression of the mean intraocular pressure (IOP) as measured in mmHg.

EXAMPLES

The following examples serve to illustrate the invention; however, these are not to be understood as restricting the scope of the invention.

Example 1: Preparation of Timolol Suspensions 109.34 mg of timolol maleate, CAS number 26921-17-5 (LKT Labs; purity 99.5%) were introduced to a 25 mL vessel, filled with stainless steel balls, diameter 2 mm. Afterwards, 8 mL of 1-perfluorohexyl-octane (F6H8) were added, the vessel was closed and the milling was performed with a planetary ball mill (PM 100, Retsch GmbH Germany) for 3 hours at 150 rpm with an interval of 10 minutes (with change of direction). After the milling, the thereby formed suspension was transferred into a glass vial, shaken on a Vortex shaker for a minimum of 30 seconds, and sealed. Considering that 1.3668 mg timolol maleate correspond to 1.0 mg timolol free base, a 1.0% (w/v) Timolol suspension (10 mg/mL) in F6H8 was obtained.

Following the same procedure as described above, a 15 mg/ml timolol suspension was prepared.

A suspension with the concentration 5 mg/mL was diluted out of the 10 mg/mL stock suspension by diluting the suspension with F6H8.

The 10 mg/mL timolol suspension was stored in a glass vial at room temperature and the particle size distribution (PSD) was determined by Laser diffraction (HELOS 2412, performed with a 50 mL cuvette). Table 1 below shows the particle size distributions for different Timolol suspensions after storage at room temperature (RT).

TABLE 1

| Formulation | $X_{50}$ (μm) | $X_{90}$ (μm) | $X_{99}$ (μm) | Conditions of storage |
|---|---|---|---|---|
| Particle size by laser diffraction (Helos H2412) performed with 50 mL cuvette and R2 lenses. (R2 lenses measurement range 0.25-87.5 μm) | | | | |
| 5 mg/mL Timolol in F6H8 | 6.02 | 10.37 | 15.53 | 2 days storage at RT |
| 10 mg/mL Timolol in F6H8 | 5.80 | 10.23 | 15.83 | 3 days storage at RT |
| 15 mg/mL Timolol in F6H8 | 6.35 | 11.25 | 16.53 | 3 days storage at RT |
| Particle size by laser diffraction (Helos H2412) with ultrasound treatment. Performed with 50 mL cuvette and R1 lenses. (R1 lenses measurement range 0.18-35 μm) | | | | |
| 5 mg/mL Timolol in F6H8 | 3.22 | 3.94 | 4.18 | 2 days storage at RT |
| 10 mg/mL Timolol in F6H8 | 3.18 | 3.92 | 4.17 | 5 days storage at RT |
| 15 mg/mL Timolol in F6H8 | 3.15 | 3.89 | 4.17 | 5 days storage at RT |

$X_{50}$: median particle diameter determined on a volumetric basis, i.e. 50% by volume of the particles are smaller than the given diameter and 50% are larger.
$X_{90}$: particle corresponding to 90% of the cumulative undersize distribution determined on a volumetric basis, i.e. 90% of the particles have a diameter lower than the given value $X_{90}$.
$X_{99}$: particle corresponding to 99% of the cumulative undersize distribution determined on a volumetric basis, i.e. 99% of the particles have a diameter lower than the given value $X_{99}$.

All Timolol suspensions in pure F6H8 with concentrations of 5 mg/ml, 10 mg/ml and 15 mg/ml, prepared by a ball milling process as described above, showed an optical appearance, homogeneity of the suspension and a suitability for re-homogenization of the settled suspensions which were ranked positive for preclinical studies in animal models.

Example 2: Measurement of Intraocular Pressure (IOP) in an Animal Study

An animal study utilizing 8 normotensive dogs was carried out in order to assess the pharmacodynamics of a composition comprising Timolol and a semifluorinated alkane with regard to its capability to lower the IOP (intraocular pressure) in comparison with a commercial solution of Timolol which is administered in form of an aqueous solution. The study setup and design was as follows.

The dogs were selected for participation in the study based on overall health, body weight, results of ophthalmic examinations, response to IOP challenge, and the following criteria:

- healthy, normal ocular surface;
- no invasive ocular procedures for at least one month prior to the study; particularly procedures involving the cornea or ocular anterior segment in general;
- no topical or systemic corticosteroid treatment for at least one month;
- washout from prior topical ocular study medication commensurate with the typical washout period used for clinical studies (at least one week)

The study was performed according to the plan as summarized in Table 2 below. The topical ocular dose of the respective Timolol aqueous solution or Timolol-suspension was administered to the central or superior part of the cornea via a micropipette and allowed to spread across the surface of the eye. After the dose was administered, the eye was allowed to close naturally. Each animal was restrained for approximately one minute to prevent rubbing of the eyes.

TABLE 2

| Topical Ocular Dose Regime | | Target Dose Level (μg/eye) | | Target Dose Volume | Dose |
|---|---|---|---|---|---|
| OD | OS | OD | OS | (μL/eye) | Frequency |
| Timolol 0.5% (5 mg/mL)* | Timolol in F6H8 (5 mg/mL) | 150 | 55 | 11 (OS) 30 (OD) | QD for 8 days |

| Topical Ocular Dose Regime | | Target Dose Level (μg/eye) | | Target Dose Volume | Dose |
|---|---|---|---|---|---|
| OS | OD | OS | OD | (μL/eye) | Frequency |
| Timolol 0.5% (5 mg/mL)* | Timolol in F6H8 (13.7 mg/mL) | 150 | 150 | 11 (OD) 30 (OS) | QD for 8 days |

*aqueous solution
OD: right eye
OS: left eye
QD: once daily
BID: twice daily

In a first study, as schematized in Table 2, a suspension of Timolol (5 mg/mL) in F6H8 was administered to the left eye versus an aqueous solution of Timolol (5 mg/mL), which was administered to the right eye. The intraocular pressure (IOP) was measured at 0 (immediately pre-dose), 2, 4 and 6 hours post-dose on days 1, 2, 3, 6 and 7; at −1, 0 (immediately pre-dose), 1, 2, 4, 6, 24 and 48 hours post-dose on day 8 using a tonometer (TonoVet). Three readings per eye were taken. The results are summarized in FIG. 1 showing the development of the mean intraocular pressure (IOP) during treatment as described above.

In a second study, as schematized in Table 2, a suspension of Timolol (13.7 mg/mL) in F6H8 was administered to the right eye versus an aqueous solution of Timolol (5 mg/mL) which was administered to the left eye. The intraocular pressure (IOP) was measured at 0 (immediately pre-dose), 2, 4 and 6 hours post-dose on days 1, 2, 3, 6 and 7; at −1, 0 (immediately pre-dose), 1, 2, 4, 6, 24 and 48 hours post-dose on day 8, using a tonometer (TonoVet). Three readings per eye were taken. The results are summarized in FIG. 2 showing the development of the mean intraocular pressure (IOP) during treatment as described above.

In a third study, 11 μl of a suspension of Timolol (5 mg/mL) in F6H8 were administered twice a day for 8 days to the left eye versus 30 μl of an aqueous solution of Timolol (5 mg/mL), which was administered to the right eye. The intraocular pressure (IOP) was measured at 0 (immediately pre-dose), 2, 4 and 6 hours post-dose on days 1, 2, 3, 6 and 7; at −1, 0 (immediately pre-dose), 1, 2, 4, 6, 24 and 48 hours post-dose on day 8, using a tonometer (TonoVet). Three readings per eye were taken. The results are summarized in FIG. 3 showing the development of the mean intraocular pressure (IOP) during treatment as described above.

The compositions according to the present invention showed a decrease of the intraocular pressure.

The invention claimed is:

1. A pharmaceutical composition consisting of particles of timolol maleate and a liquid vehicle; wherein the particles consist of the timolol maleate, and wherein the particles are suspended in the liquid vehicle; wherein the liquid vehicle consists essentially of 1-perfluorohexyloctane and optionally a co-solvent; wherein at least 90% of the suspended particles of the timolol maleate have a size of not more than about 20 μm; wherein the concentration of the timolol maleate in the pharmaceutical composition corresponds to about 0.5% (w/v) of timolol, measured as the free base; and wherein the composition is formulated for topical ophthalmic administration.

2. The pharmaceutical composition according to claim 1, wherein the liquid vehicle further comprises the co-solvent.

3. The pharmaceutical composition according to claim 1, wherein the liquid vehicle consists essentially of the 1-perfluorohexyloctane.

4. The pharmaceutical composition of claim 1, wherein at least about 90% of the suspended particles of the timolol maleate have a size of not more than about 15 μm.

5. The pharmaceutical composition according to claim 1, wherein the pharmaceutical composition provides a dose volume per eye of from about 10 to about 12 μl which comprises about 55 μg timolol, measured as the free base.

6. A method for the treatment of glaucoma, increased intraocular pressure, ocular hypertension and/or a symptom associated therewith, in a patient in need thereof, comprising administering to said patient a pharmaceutical composition according to claim 1, wherein the composition is topically administered to the eye of the patient at a single dose of about 55 μg timolol, measured as the free base, per eye.

7. The method according to claim 6, wherein the pharmaceutical composition is administered to the eye of the patient up to four times daily.

8. The method according to claim 6, wherein the pharmaceutical composition is administered to the eye of the patient two times daily or once daily.

9. The method according to claim 6, wherein the pharmaceutical composition is administered in a dose volume per eye of from about 10 to about 12 μl.

10. The method according to claim 6, wherein the liquid vehicle further comprises the co-solvent.

11. The method according to claim 6, wherein the liquid vehicle essentially consists of the 1-perfluorohexyloctane.

12. The method according to claim 6, wherein the pharmaceutical composition is topically administered to the eye of the patient at a single dose of 55 μg timolol, measured as the free base, per eye.

13. The method according to claim 6, wherein the pharmaceutical composition is administered in a dose volume per eye of from about 11 μl.

14. The method according to claim 11, wherein the pharmaceutical composition is topically administered one time daily to the eye of the patient at a single dose of 55 μg timolol, measured as the free base, per eye.

15. The method according to claim 11, wherein the pharmaceutical composition is topically administered two times daily to the eye of the patient at a single dose of 11 μl per eye.

16. The method according to claim 6, wherein the pharmaceutical composition is free of water and free of a preservative.

17. The method according to claim 6, wherein at least about 90% of the suspended particles of timolol maleate have a size of not more than about 10 μm.

18. The method according to claim 6, wherein at least about 90% of the suspended particles of timolol maleate have a size of not more than about 15 μm after three weeks of storage at room temperature.

19. The composition according to claim 1, wherein the liquid vehicle consists essentially of at least 99.5% (w/w) 1-perfluorohexyloctane, with respect to the total weight of the liquid vehicle.

20. The method according to claim 16, wherein the pharmaceutical composition is a preservative-free ophthalmic composition, that is provided in a microbiologically stable multi-dose or single dose format.

21. The method according to claim 16, wherein the method comprises the step of redispersing the particles of timolol maleate by gently shaking the container holding the composition before topically administering the composition to the eye.

* * * * *